US007906281B2

(12) United States Patent
Kelsoe

(10) Patent No.: US 7,906,281 B2
(45) Date of Patent: Mar. 15, 2011

(54) METHOD TO PREDICT THE RESPONSE TO LITHIUM TREATMENT

(75) Inventor: John R. Kelsoe, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 121 days.

(21) Appl. No.: 11/544,065

(22) Filed: Oct. 6, 2006

(65) Prior Publication Data

US 2007/0122825 A1 May 31, 2007

Related U.S. Application Data

(60) Provisional application No. 60/728,432, filed on Oct. 7, 2005.

(51) Int. Cl.
*C12Q 1/68* (2006.01)
*C12P 19/34* (2006.01)
*C07H 21/02* (2006.01)

(52) U.S. Cl. .................... 435/6; 435/91.2; 536/23.1

(58) Field of Classification Search .................. None
See application file for complete search history.

(56) References Cited

U.S. PATENT DOCUMENTS

| | | | |
|---|---|---|---|
| 2002/0077756 A1 | 6/2002 | Arouh et al. | |
| 2003/0204319 A1 | 10/2003 | Arouh et al. | |
| 2003/0204320 A1 | 10/2003 | Arouh et al. | |
| 2004/0030503 A1 | 2/2004 | Arouh et al. | |
| 2004/0053257 A1* | 3/2004 | Kelsoe, Jr. et al. | 435/6 |
| 2005/0069936 A1 | 3/2005 | Diamond et al. | |
| 2005/0176057 A1* | 8/2005 | Bremer et al. | 435/6 |
| 2006/0129324 A1 | 6/2006 | Rabinoff et al. | |

OTHER PUBLICATIONS

Barrett (Barrett et al; Molecular Psychiatry, vol. 8, pp. 546-557, 2003).*
Couzin et al. (Science 2008 vol. 319 p. 274).*
Kelsoe et al. (UCSD Genetic Predictors of Response to Lithium in Bipolar Disorder Oct. 9, 2004).*
Prata et al. (Psychiatric Genetics 2006 vol. 16 p. 229).*
Aarons, S. et al., "A regulatory RNA (PrrB RNA) modulates expression of secondary metabolite genes in Pseudomonas fluorescens F113," Journal of Bacteriology, 182 (14):3913-3919 (2000).
Anwar et al., "Susceptibility of biofilm cells of Pseudomonas aeruginosa to bactericidal actions of whole blood and serum," FEMs microbial. Let. 71:235-241 (1992).
Barta et al., "Regulation of tabtoxin production by the lemA gene in Pseudomonas syringae," J. Bacteriol. 174:3021-3029 (1992).
Blumer, D., et al., Multicopy suppression of a gacA mutation by the infC operon in Pseudomonas fluorescens CHA0: competition with the global translational regulator RsmA, FEMS Microbiology Letters, 187:53-88 (2000).
Blummer et al., "Global GacA-steered control of cyanide and exoprotease roduction in Pseudomonas fluorescens involves specific ribosome binding sites," Proc. Natl. Adad, Sci. USA, 96:14073-14078 (1999).
Boyd et al., "Pseudomonas aeruginosa biofolms; role of alginate exopolysaccharide," J. Ind. Microbial. 15:162-168 (1995).
Bradley, "A function of Pseudomonas aeruginosa PAO pili: twitching motility," Can. J. Microbiol, 26:146-154 (1980).
Brinkman, F. et al., "Evolutionary relationships among virulence-associated histidine kinases, Infection and Immunity," 69:5207-5211 (2001).
Bullock, W.O. et al., "E. coli XL-Blue: a high efficiency plasmid transforming recA Eschenchia coli strain with beta-galactosidase selection," Biotechniques, 5:376-378 (1987).
Castaneda et al., "The GacS sensor kinase regulates alginate and poly-beta-hydroxybuyrate production in Azotobacter vinelandii," J. Bacterial 182:2624-2628 (2000).
Ceri et al., "The Calgary Biofilm Device: A new technology for the rapid determination of antibiotic susceptiability of bacterial biofilms;" J. Clin, Microbiol. 37:1771-1776 (1999).
Ceri et al., "The MBEC Assay System: multiple equivalent biofilms for antibiotic and biocide susceptibility," Methods Enzymol, 337:377-384 (2001).
Chancey et al., "Two-component transcriptional regulation of N-acyl-homserine lactone production in Pseudomonas aureofaciens," Appl. Environ. Microbial., 65:2294-2299 (1999).
Chancey et al., "Survival of GacS/GacA mutants of the biological control bacterium Pseudomonas aureofaciens 30-84 in the wheat rhizosphere," Appl. Environ. Microbiol., 68(7):3308-14 (2002).
Corbell, N. et al. "A global regulator of secondary metabolite production in Pseudomonas fluorescens Pf-5," J. Bacteriol. 177, 6230-6236 (1995).
Costerton et al.., "Microbial biofilms," Annu. Rev. Microbial., 49:711-745 (1995).
Costerton et al., "Bacterial biofoms: a common cause of persistent infections," Science, 284:1318-1322 (1999).
Davies et al., "The involvement of cell-cell signals in the development of a bacterial biofilm," Science, 280:295-298 (1998).
Deziel, E, et al., "Initiation of biofilm formation by Psedomonas aeruginosa 57RP correlates with emergence of hyperpiliated and highly adherent phenotypic variants deficient in swimming, swarming, and twitching motilities," Journal of Bacteriology, 183:1195-1204 (2001).
Drenkard, E. et al., "Pseudomonas biofilm formation and antibiotic resistance are linked to phenotypic variation," Nature 416:740-743 (2002).
Duffy, B. et al., "Controlling instability in gacS-gacA regulatory genes during inoculant production of Pseudomonas fluorescens biocontrol strains," Applied and Environmental Microbiology, 66:3142-3150 (2000).
Dybvig, K. et al., "DNA rearrangements and phenotypic switching in prokaryotes," Molecular Microbiology, 10:465-471 (1993).
Ellard, J , The NEB Transcript, 6:7 (1994).
Frank et al., "Kinetics of toxA and regA mRNA accumulation in Pseudomonas aeruginosa," J. Bacteriol. 170:4477-4483 (1988).
Gambello et al., "Cloning and characterization of the Pseudomonas aeruginosa lasR gene, a transcriptional activator of elastase expression," J. Bacteriol 173:3000-3009 (1991).
Gault, M.H. et al. "Staphylococcal epidermidis infection of a hemodialysis button-graft complex controlled by vancomycin for 11 months," Nephron, 45:126-128 (1987).

(Continued)

*Primary Examiner* — Sarae Bausch
*Assistant Examiner* — Katherine Salmon
(74) *Attorney, Agent, or Firm* — Joseph R. Baker, Jr.; Gavrilovich Dodd & Lindsey LLP

(57) ABSTRACT

The disclosure provides methods and compositions useful for identifying a subject's predisposition to lithium treatment.

19 Claims, 2 Drawing Sheets

OTHER PUBLICATIONS

Gomez-gomez, J. et al., "H-NS and RpoS regulate emergence of Lac Ara mutants of *Escherichia coli* MCS2," Journal of Bacteriology, 179(14):4620-4622 (1997).

Grewal et al., "Identification and characterization of a locus which regulates multiple functions in *Pseudomonas tolaasii*, the case of brown blotch disease of *Agaricus bisporus*," J. Bacteriol., 177:4658-4668 (1995).

Han, B. et al., "Spontaneous duplication of a 661 bp element within a two-component sensor regulator gene causes phenotypic switching in colonies of *Pseudomonas tolaasii*, cause of brown blotch disease of mushrooms," Molecular Microbiology, 25:211-218 (1997).

Hass, D. et al., "Signal transduction in plant-beneficial rhizobacteria with biocontrol properties," Antonie van Leeuwenhoek, 81:385-395 (2002).

Heeb, S. et al., "Regulatory roles of the G-asS/GasA two-component system in plant-associated and other gram-negative bacteria," Molecular Plant-Microbe Interactions, 14:1351-1363 (2001).

Henderson, I. et al., "Molecular switches—the ON and OFF of bacterial phase variation," Molecular Microbiology, 33:919-932 (1999).

Heydorn, A. et al., "Statistical analysis of *Pseudomonas aeruginosa* biofilm development: impact of mutations in genes involved in twitching motility, cell-to-cell signaling, and stationary-phase sigma factor expression," Applied and Environmental Microbiology, 68(4):2008-2017 (2002).

Hirano et al., "Role of Hrp type III secretion system in growth of *Pseudomonas syringae pv. Syringae* B728a on host plants in the field," Proc. Natl, Acad. Sci. USA, 96:9851-9856 (1999).

Hoang, T. et al., "A broad-host-range Flp-Frt recombination system for site-specific excision of chromosomally-located DNA sequences: applications for isolation of unmarked *Pseudomonas aeruginosa* mutants," Gene, 212:77-86 (1998).

Holloway et al., "Chromosomal genetics of *Pseudomonas*," Microbial. Rev. 43:73-102 (1979).

Horii, T. et al., "Relationship between morphological changes and endotoxin release induced by carbapenems in *Pseudomonas aeruginosa*," Journal of Medical Mibrobiology, 48:309-315 (1999).

Hrabak et al., "The lemA gene required for pathogenicity of *Pseudomonas syringae pv. Syringae* on bean is a member of a family of two-component regulators," J. Bacteriol, 174:3011-3020 (1992).

Jander et al., Positive correlation between virulence of *Pseudomonas aeruginosa* mutants in mice and insects. J. Bacteriol. 182:3843-3845 (2000).

Jensen et al., "Human polymorphonuclear leukocyte response to *Pseudomonas aeruginosa* grown in biofilms," Infect. Immun. 58:2383-2385 (1990).

Jensen et al., "Complement activation by *Pseudomonas aeruginosa* biofolms" Microbiol, Path., 15:377-388 (1993).

Jenson et al., "Some bacterial parameters influencing the neutrophil oxidative burst response *Pseudomonas aeruginosa* biofilms," APMIS, 100:727-733 (1992).

Johnston et al., "Transcriptional activation of *Salmonella typhimurium* invasion genes by a member of the phosphorylated response-regulator superfamily," Mol. Microbiol. 22:715-27 (1996).

Kim, Y.C. et al., "Identification of adjacent genes encoding the major catalase and a bacterioferritin from the plant-beneficial bacterium *Pseudomonas putida*," Gene, 199:219-224 (1997).

Kim et al., "Sensor kinase GacS regulates production of quorum sensing factors, secondary metabolites and root colonization in *Pseudomonas* chlororaphis O6," Phytopathology, 91:S49 (2001).

King, E.O. et al., "Two simple media for the demonstration of pyocyanin and fluorescin," J Lab Clin Med, 44:301-307 (1954).

Kinscherf et al., "Swarming by *Pseudomonas syringae* B728a requires gacS (lemA) and gacA but not the acyl homoserine lactone biosynthetic gene ahlI," J. Bacterial. 181:4133-4136 (1999).

Kitten et al., "A newly identified regulator is required for virulence and toxin production in *Pseudomonas syringae*," Mol. Microbiol. 28:917-929 (1998).

Kitten, T. et al., "Suppression of a sensor kinase-dependent phenotype in *Pseudomonas syringae* by ribosomal proteins L35 and L20," Journal of Bacteriology, 178:1548-1555 (1996).

Kleerebezem, M. et al., "Quorum sensing by peptide pheromones and two-component signal-transduction systems in Gram-positive bacteria," Molecular Microbiology, 24:895-904 (1997).

Koch, B, et al., "Lipopeptide production in *Pseudomonas sp*. Strain DSS73 is regulated by components of sugar beet seed exudate via the Gac two-component regulatory system," Applied and Environmental Microbiology, 68(9):4509-4516 (2002).

Kohler et al., "Swarming of *Pseudomonas aeruginosa* is dependent on cell-to-cell signaling and requires flagella and pili," J. Bacteriol. 182:5990-5996 (2000).

Kropp et al., "Increased emergence fo spring wheat after inoculation with *Pseduomonas* chlororaphis isolate 2E3 under field and laboratory conditions," Biol. Fertil. Soils, 23:200-206 (1996).

Lam et al., "Production of mucoid microcolonies by *Pseudomonas aeruginosa* within infected lungs in cystic fibrosis," Infect. Immun. 28:546-556 (1980).

Liao et al., "Molecular characterization of two gene loci required for production of the key pathogenicity factor for pectate lyase in *Pseudomonas viridiflava*," Mol. Plant—Microbe Interact. 7:391-400 (1994).

Liao et al., "The repB gene required for production of extracellular enzymes and fluorescent siderophores in *Pseudomonas viridiflava* is an analog of the gacA gene in *Pseudomonas syringae*," Can, J. Microbiol. 42:177-182 (1996).

Liss et al., "New M13 host:DH5αF' competent cells," Focus 9:13 (1987).

Mahajan-Miklos et al., "Molecular mechanisms of bacterial virulence elucidated using a *Pseudomonas aeruginosa—Caenorbabditis elegans* pathogenesis model," Cell, 96:47-56 (1999).

Marrie, T.J., "A scanning electron microscopic study of urine droppers and urine collecting systems," Archives of Internal Medinice, 143:1135-1141 (1983).

Marrie, T.J. et al., "Scanning and transmission electron microscopy of in situ bacterial colonization of intravenous and intraarterial catheters," Journal of Clinical Microbiology, 19:687-693 (1984).

Mascher, F. et al., "Inactivation of the regulatory gene algU or gacA can affect the ability of biocontrol *Pseudomonas fluorescens* CHA0 to persist as culturable cells in nonsterile soil," Applied and Environmental Microbiology, 68:2085-2088 (2002).

May et al., "Isolation and assay of *Pseudomonas aeruginosa* alginate," Method in enzymology, 235:295-304 (1994).

Meluleni et al., "Mucoid *Pseudomonas aeruginosa* growing in a biofilm in vitro are killed by opsonic antibodies to the mucoid exopolysaccharide capsule but not antibodies produced during chronic lung infection in cystic fibrosis patients," J. Immunol., 155:2029-2038 (1995).

McClean et al., "Quorum sensing and Chromobacterium violaceum: exploitation of violacein production and and inhibition for the detection of N-acyl homoserine lactones," Microbiol, 143:3703-3711 (1997).

Monzon, M et al., "Synergy of different antibiotic combinations in biofilms of *Staphylococcus epidermidis*," The Journal of Antimicrobial Chemotherapy, 48:793-801 (2001).

Morck, D.W. et al., "Microbial biofilms: prevention, control, and removal," In *Disinfection, Sterilization and Preservation*, Block S.S. (ed), 673-681 (2001).

Mosteller, T.M. et al., "Sanitizer efficacy against attached bacteria in a mild biofilm," Journal of Food Protection, 56:34-41 (1993).

Nichols et al., "The penetration of antibiotics into aggregates of mucoid and non-mucoid *Pseudomonas aeruginosa*," J. Gen. Microbiol., 135:1291-1303 (1989).

Nickel, C.J. et al., "Electron microscopic study of an infected foley catheter," The Canadian Journal of Surgery, 28: 50-52 (1985).

Nickel, C.J. et al., "Bacterial biofilm in persistent penile prosthesis-associated infection," Journal of Urology, 135:586-588 (1986).

Oilos, P.J. et al. "Bench scale investigations of bacterial regrowth in drinking water distribution systems," Water Science & Technology, 38:275-282 (1998).

O'Sullivan et al., "Traits of fluorescent *Pseudomonas* spp. Involved in suppression of plant root pathogens," Microbiol. Rev. 56:662-676 (1992).

O'Toole, G. et al., "Biofilm formation as microbial development," Annual Review of Microbiology, 54:49-79 (2000).

O'Toole et al., "Initiation of biofilm formation in *Pseudomonas flourescens* WCS365 proceeds via multiple, convergent signaling pathways: a genetic analysis," Mol. Microbiol., 28:449-461 (1998).

O'Toole et al., "Flagellar and twitching motility are necessary for *Pseudomonas aeruginosa* biofilm development," Mol. Microbiol., 30:295-304 (1998).

O'Toole et al., "The global carbon metabolism regulator Cre is a component of a signal transduction pathway required for biofilm development by *Pseudomonas aeruginosai*" J. Bacterial., 182:425-431 (2000).

Parkins et al., "*Pseudomonas aeruginosa* GacA, a factor in multihost virulence, is also essential for biofilm formation," Molecular Microbiology, vol. 40, No. 5, pp. 1215-1226, (2001).

Parkins, M.D., "Gene expression in *Pseudomonas aeruginosa* biofilms," MSc Thesis, University of Calgary (2000).

Pearce et al., "The rhizosphere as a biofilm," In Microbial Biofilms, Lappin-Scott et al. eds. Cambridge University Press, Cambridge, UK. pp. 207-220.

Pearson et al., "Structure of the autoinducer required for the expression of *Pseudomonas aeruginosa* virulence genes " Proc. Natl. Acad. Sci. USA 91:197-201 (1994).

Pearson et al., "Roles of *Pseudomonas aeruginosa* las and rhl quorum sensing systems in control of elastase and rhamnolipid biosynthesis genes," J. Bacteriol., 179:5756-5767 1997.

Percival, S.L. et al., "Biofilms mains water and stainless steel," Water Research, 32:2187-2201 (1998).

Pesci et al., "Regulation of las and rhl quorum-sensing in *Pseudomonas aeruginosa*," J. Bacteriol., 179:3127-3132 (1997).

Pessi, G. et al., "Dual control of hydrogen cyanide biosynthesis by the global activator GasA in *Pseudomonas aeruginosa* PA01," FEMS Microbiology Letters, 200(1):73-8 (2001).

Pierson III et al, "Homoserine lactone-mediated gene regulation in plant-associated bacteria," Annu. Rev. Phytopathol, 36:207-225 (1998).

Plumb, D.C., *Veterinary Drug Handbook*, Fourth Edition, Iowa State Press, p. 632 (2002).

Pratt et al., "Genetic analysis of *Escherichia coli* biofilm formation: roles of flagella, motility, chemotaxis and type I pili," Mol. Microbiol., 30:285-293 (1998).

Radtke et al., Factors affecting antagonism of growth of *Phanerochaete chyrsosporium* by bacteria isolated from soils. Appl. Microbiol. Biotechnol. 41:274-280 (1994).

Rahme et al. , "Common virulence factors for bacterial pathogenicity in plants and animals," Science. 268:1899-1902 (1995).

Rahme et al., "Use of model plant hosts to identify *Pseudomonas aeruginosa* virulence factors," Proc. Natl. Acad. Sci. USA, 94:13245-13250 (1997).

Rahme et al., "Plants and animals share functionally common bacterial virulence factors," Proc. Natl. Acad. Sci. USA, 97:8815-8821 (2000).

Rashid, M. et al., "Inorganic polyphosphate is needed for swimming, swarming, and twitching motilities of *Pseudomonas aeruginosa*," Proceedings of the National Academy of Science USA, 97:4885-4890 (2000).

Rashid et al., "Polyphosphate kinase is essential for biofilm development, quorum sensing, and virulence of *Psedomonas aeruginosa*," Proc. Natl. Acad. Sci. USA, 97:8815-8821 (2000).

Reimmann et al., "The global activator GacA of *Pseudomonas aeruginosa* PAO positively controls the production of the autoinducer N-butyryl-homoserine lactone and the formation of the virulence factors pyocyanin, cyanide and lipase," Mol. Microbiol., 24:309-319 (1997).

Rich et al., "Genetic eveidence that the gacA gene encodes the cognate response regulator for the lemA sensor in *Pseudomonas syringae*," J. Bacterial., 176;7468-7475 (1994).

Riosen, P.A. et al., "Identification of the DNA-binding sites for two response regulators involved in control of bacteriocin synthesis in Lactobacillus plantarum C11," Molecular and General Genetics, 259:224-232 (1998).

Rumbaugh et al., "Contribution of the regulatory gene lasR to the parthogenesis of *Pseudomonas aeruginosa* infection of burned mice," J. Burn Car Rehabil., 20:42-49 (1999).

Rumbaugh et al., "Contribution of quorum sensing to the virulence of *Pseudomonas aeruginosa* in burn wound infections," Infect. Immure 67:5854-5862 (1999).

Seleh, S. et al., "Involvement of gacS and rpoS in enhancement of the plant growth-promoting capabilities of Enterobacter cloacae CAL2 and UW4," Canadian Journal of Microbiology, 47:698-705 (2001).

Sambrook, J. et al., "Molecular Cloning: A Laboratory Manual," Cold Spring Harbor Laboratory Press (1989).

Sanchez-Contreras, M. et al., "Phenotypic selection and phase variation occur during alfalfa root colonization by *Pseudomonas fluorescens* F113," Journal of Bacteriology, 184:1587-1596 (2002).

Schweizer, H. "Allelic exchange in *Pseudomonas aeruginosa* using novel ColE1-type vectors and a family of cassettes containing a portable oriT and the counter-selectable *Bacillus subtilis* sacB marker," Molecular Microbiology, 6(9):1195-1204 (1992).

Schweizer, H., "*Escherichi-Pseudomonas* shuttle vectors derived frompUC18/19," Gene, 97:109-112 (1991).

Schweizer, H., "Small broad-host-range gentamycin resistance gene cassettes for site-specific insertion and deletion mutagenesis," BioTechniques, 15(5):831-832 (1993).

Schwyn, B. et al., "Universal chemical assay for the detection and determination of siderophores," Anal. Biochem. 160:47-56 (1987).

Seed et al., "Activation of the *Pseudomonas aeruginosa* lasI gene by LasR and the *Pseudomonas* autoinducer Pal; and Autoinduction regulatory hierarchy" J. Bacteria, 177:654-659 (1995).

Semmler et al., "A re-examination of twitching motility in *Pseudomonas aeruginosa*," Microbiol., 145:2863-2873 (1999).

Seveno, N. A. et al., "Growth of *Pseudomonas aereofasciens* PGS12 and the dynamics of HHL and phnezine production in liquid culture, on nutrient agar and on plant roots," Microb. Ecol., 41:314 (2001).

Simon, R et al., "A broad host range mobilization system for in vivo genetic engineering: transposon mutagenesis in gram negative bacteria," Biotechnology, 1:784-791 (1983).

Singh et al., "Quorum-sensing signals indicate that cystic fibrosis lungs are infected with bacterial biofilms," Nature, 407:762-764 (2000).

Smith et al., "Transformation of *Pseudomonas aeruginosa* by electroporation," Nucl. Acids Res. 17:10509 (1989).

Snyder, L. et al., "Global regulatory mechanisms In: Molecular Genetics of Bacteria," American Society for Microbiology, 309 (1997).

Stock, A.M. et al. "Two-component signal transduction," Annual Reviews Biochemistry, 69:183-215 (2000).

Strathmann, M. et al., "Application of fluorescently labeled lectins for the visualization and biochemical characterization of polysaccharides in biofilms of *Pseudomonas aeruginosa*," Journal of Microbiological Methods, 50:237-248 (2002).

Stewart, "Biofilm accumulation model that predicts antibiotic resistance of *Pseudomonas aeruginosa* biofilms," Antimicrob. Agents Chemother., 38:1052-1058 (1994).

Stover et al., "Complete genome sequene of *Pseudomonas aeruginosa* PA01, an opportunistic pathogen," Nature, 406:959-964 (2000).

Suci et al.., "Investigation of ciprofloxacin penetration into *Pseudomonas aeruginosa* biofilms,"Antimicrob. Agents. Chemother., 35:2125-2132 (1994).

Tan et al., "Killing of *Caenorhabditis elegans* by *Pseudomonas aeruginosa* used to model mammalian bacterial pathogenesis," Proc. Natl. Acad. Sci. USA, 96:715-720 (1999).

Tan et al., "*Pseudomonas aeruginosa* killing of *Caenorhabditis elegans* used to identify *P. aeruginosa* virulence factors," Proc. Natl Acad. Sci, USA, 96:2408-2413 (1999).

Tang et al., "Contribution of specific *Pseudomonas aeruginosa* virulence factors to pathogenesis of pneumonia in a neonatal mouse model of infection," Infect Immun., 64:37-43 (1996).

Tombolini, R. et al., "Colonization pattern of the biocontrol strain *pseudomonas* chlororaphis MA342 on barley seeds visualized by using green fluorescent proteins," Appl. Environm. Microbiol., 65:3674-3680 (1999).

Tortosa, P. et al., "Competence for transformation: a matter of taste," Current Opinions in Microbiology, 2:588-592 (1998).

University of Calgary Animal Health Unit SOP IL: Immunization, Feb. 1994.

Van Beldon, C. et al., "Cell-to-cell signalling and *Pseudomonas aeruginosa* Infections," Emerging Infectious Diseases, 4:551-560 (1998).

Vogel, H.J. et al., "Acetylornithinase of *Escherichia coli*: partial purification and some properties," The Journal of Biological Chemistry, 218:97-106 (1956).

Walters, M. et al., "Contributions of antibiotic penetration, oxygen limitation, and low metabolic activity to tolerance of *Pseudomonas aeruginosa* biofilms to ciprofloxacin and tobramycin," Antimicrobial Agents and Chemotherapy, 47(1):317-323 (2003).

Ward, K. et al., "Mechanism of persistent infection associated with peritoneal implants," Journal of Medical Microbiology, 36:406-413 (1992).

Whistler et al,, "The two component regulators GacS and GacA influence accumulation of stationary phase sigma factor oS and the stress reponse in *Pseudomonas fluorescens* Pf-5," J. Bacteriol., 180:6635-6641 (1998).

Whiteley, M. et al., "Gene expression in *Pseudomonas aeruginosa* biofilms," Nature, 413:860-864 (2001).

Willis, D.K. et al., "Isolation and characterization of a *Pseudomonas syringae pv. Syringae* mutant deficient in lesion formation on bean," Molecular Plant-Mibrobe Interations, 3:149-156 (1990).

Wohleben, W. et al., On the evolution of Tn21 multiresistance transposons. Sequence analysis of the gene (aaaC1) for gentamicin acetyltransferase-3-I(AAC(3)-I), another member of the Tn21-based expression cassette Molecular and General Genetics, 217:202-208 (1989).

Yanisch-Perron, C. et al., "Improved M13 phage cloning vectors and host strains:. nucleotide sequences of the M13mp18 and pUC19 vectors," Gene, 33:103-119 (1985).

Yanks, S. et al., "Serum immune response to Girardia duodenalis in experimentally infected lambs," Veterinary Parasitology, 75:9-19 (1998).

Zhang et al., "Induction of gene expression in *Escherichia coli* after pilus mediated adherence," Science, 273:1234-1236 (1996).

Zhang et al., "A scond quorum-sensing system regulates cell surface properties but not phenazine antibiotic production in *Pseudomonas aureofasciens*," Appl. Envrionm. Microbiol., 67:4305-4315 (2001).

Nurnberger, John I., Psychiatric Genetics 15(2):79-80, Jun. 2005.

Kelsoe, John R., Rebecca McKinney, Tatyana Shekhtman, Heghan Gaucher and Geraldine Smith, "Genetic Preditors of Response to Lithium in Bipolar Disorder" Abstract to the World Congress on Psychiatric Genetics Oct. 9-12, 2004.

Stambolic, Vuk, Laurent Ruel and James R. Woodgett, "Lithium inhibits glycogen synthase kinase-3 activity and mimics Wingless signalling in intact cells" Current Biology, vol. 6, No. 12., pp. 1664-1668, 1996.

\* cited by examiner

METHOD TO PREDICT THE RESPONSE TO LITHIUM TREATMENT

CROSS REFERENCE TO RELATED APPLICATIONS

The application claims priority under 35 U.S.C. §119 to U.S. Provisional Application Ser. No. 60/728,432, filed Oct. 7, 2005, the disclosure of which is incorporated herein by reference.

TECHNICAL FIELD

The invention relates to predicting the probability that a patient with bipolar disorder will have a beneficial therapeutic response to the medication lithium.

BACKGROUND

Presently, there are no biological tests in clinical use to predict a patient's response to lithium. Many patients have a very good response in terms of the stabilization of their mood, while other patients may respond better to different medications. As a result, it is typical that many medications may need to be tried before an effective one is identified.

SUMMARY

This invention provides methods, compositions, systems and kits useful for predicting a response to lithium treatment in a subject. The invention uses techniques and compositions that measure the presence or absence of certain single nucleotide polymorphisms (SNPs) in GRK3, NTRK2, IMPA genes.

The invention provides a method of determining a probability of response of a subject of known clinical history to a pharmaceutical agent for a mood disorder, the method comprising: correlating (i) a mutational burden at one or more nucleotide positions in genes drawn from the group consisting essentially of ADRBK2, BNDF, GSK3B, GRK3, IMPA1, IMPA2, INPP1, MARCKS, NTRK2 and/or NR1I2 within a sample taken from the subject of known clinical history with (ii) a mutational burden at one or more corresponding nucleotide positions in a control sample having known clinical history and response outcomes to the pharmaceutical agent; and determining from the correlating the probability of response of the subject to the pharmaceutical agent.

The invention provides a method comprising (a) providing a sample comprising polynucleotides obtained from a subject; (b) contacting the sample with at least one probe comprising at least 8 contiguous nucleotides of SEQ ID NO:1, 2, 7 or 8 and containing nucleotide 26 or the complement thereof; and (c) determining if the sample comprises a polynucleotide molecule that hybridizes to the at least one probe. In one aspect, the method further comprises diagnosing a mental disorder or clinical symptom in the subject selected from the group consisting of euphoric mania, dysphoric mania, Bipolar I, Rapid Cycling, History of Suicide Attempt, PTSD, Panic Attacks/Panic Disorder, Alcohol or Substance Dependence, and any combination thereof.

The invention also provides a method for determining whether a subject comprising a mental or mood disorder is responsive to lithium, comprising contacting a sample with at least one probe comprising at least 8 contiguous nucleotides of SEQ ID NO:1-15 or 16, and containing nucleotide 26 or the complement thereof; and determining if the sample comprises a polynucleotide molecule that hybridizes to the probe.

In one aspect, the method further comprises diagnosing a mental disorder or clinical symptom in the subject selected from the group consisting of euphoric mania, dysphoric mania, Bipolar I, Rapid Cycling, History of Suicide Attempt, PTSD, Panic Attacks/Panic Disorder, Alcohol or Substance Dependence, and any combination thereof.

The invention provides a method of determining a subject's response to lithium comprising detecting at least on polymorphism in a gene selected from the group consisting of NTRK2, GRK3, IMPA1 and IMPA2 wherein the polymorphism is selected from the group consisting of rs133845, rs11913984, rs1187287, rs1387923, rs1565445, rs1187352, rs971363 and rs915.

The invention also provides an isolated oligonucleotide comprising a sequence selected from the group consisting of: SEQ ID NO:1 or 2 having at least 8 nucleotide and containing nucleotides 25-27; SEQ ID NO:3 or 4 having at least 8 nucleotide and containing nucleotides 25-27; SEQ ID NO:5 or 6 having at least 8 nucleotide and containing nucleotides 25-27; SEQ ID NO:7 or 8 having at least 8 nucleotide and containing nucleotides 25-27; SEQ ID NO:9 or 10 having at least 8 nucleotide and containing nucleotides 25-27; SEQ ID NO:11 or 12 having at least 8 nucleotide and containing nucleotides 25-27; SEQ ID NO:13 or 14 having at least 8 nucleotide and containing nucleotides 25-27; and SEQ ID NO:15 or 16 having at least 8 nucleotide and containing nucleotides 25-27. The oligonucleotide can be immobilized on a solid support.

The invention also provides a kit compartmentalized to receive a reagent for measuring mutational burden in the genes of a subject, wherein the reagent comprises an oligonucleotide probe or primer that measures a polymorphism in a gene selected from the group consisting of ADRBK2, BNDF, GSK3B, GRK3, IMPA1, IMPA2, INPP1, MARCKS, NTRK2 and/or NR1I2.

The details of one or more embodiments are set forth in the accompanying drawings and the description below. Other features, objects, and advantages will be apparent from the description and drawings, and from the claims.

DETAILED DESCRIPTION

Figure 1:
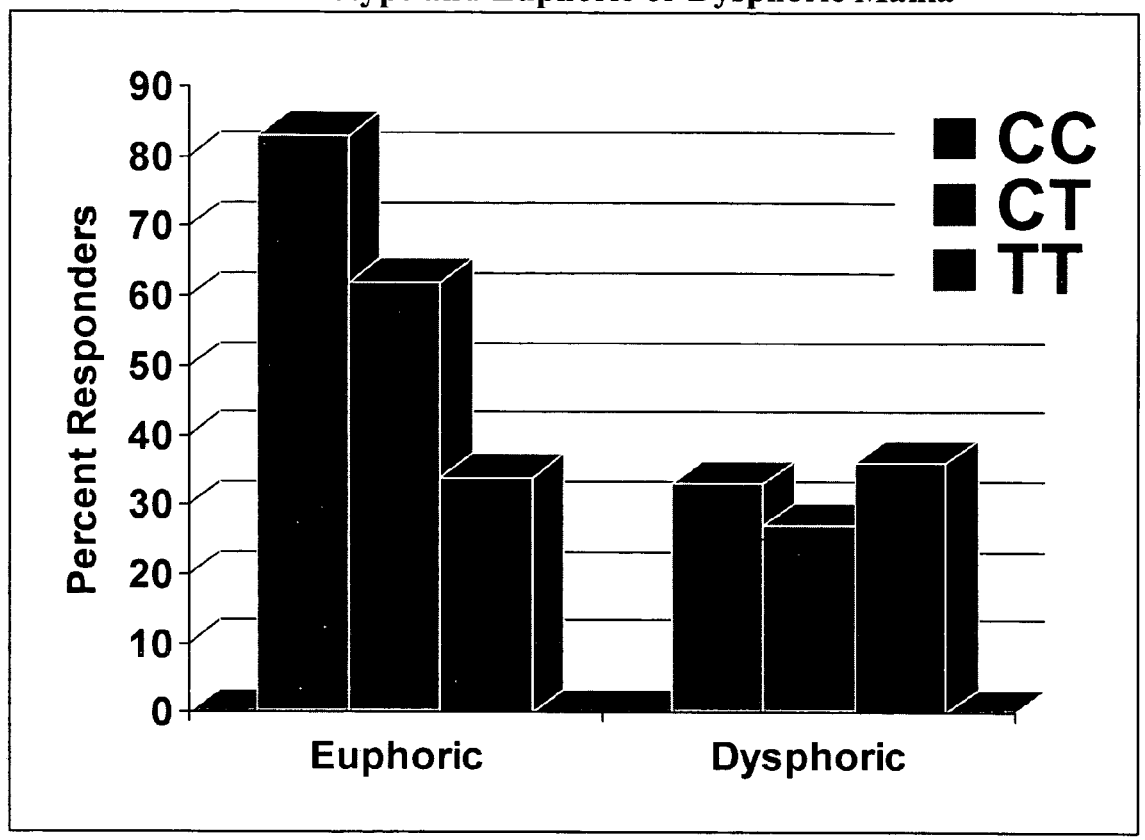
FIG. 1 shows that an NTRK2 genotype is associated with lithium response. NTRK2 genotypes CC, CT, TT in SNP rs1387923 are minor homozygote, heterozygote and major homozygote, respectively.

As used herein and in the appended claims, the singular forms "a," "and," and "the" include plural referents unless the context clearly dictates otherwise. Thus, for example, reference to "a polynucleotide" includes a plurality of such polynucleotides and reference to "the SNP" includes reference to one or more SNPs known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

One of the greatest clinical challenges in treating bipolar disorder is that of selecting the appropriate agent. In usual clinical practice, this is largely trial and error, or drugs are chosen based on side effect profiles. There is concern that many patients may never be tried on the agent that would best benefit them. There is also great need for any predictor that would aid clinicians in these difficult choices. The invention provides methods and systems for detecting genetic variation providing guidance on a suitable drug therapy.

Lithium is the first mood stabilizer and the one for which there exists the most efficacy data. Though most patients with bipolar disorder respond well, others fail to respond or to tolerate its side effects. Largely because of side effects, its use has been supplanted in some countries by other agents. It has been argued that genetic factors may be important in determining response. A pharmacogenetic panel of DNA tests capable of predicting response would be of great clinical value in optimizing the treatment of bipolar disorder.

The discovery of lithium revolutionized the treatment of bipolar disorder by providing a specific treatment for mania and prophylaxis for mania and depression. In recent years, several anticonvulsants and antipsychotics have also shown both acute and chronic mood stabilizing efficacy, providing a number of choices for the pharmacological treatment of bipolar disorder. It is not unusual, though, for patients to require trials of several drugs before optimum treatment is identified. This is, in part, due to side effects and medication tolerance, but it also reflects an individual variability in response. As each trial may take several months, multiple trials to identify the best regimen may require months to years, thereby extending patient suffering and lost productivity. A method to predict response for individual patients would be of great clinical utility.

Euphoric mania reportedly predicts good response to lithium, whereas dysphoric mania, irritable mania or mixed states may predict better response to anticonvulsant mood stabilizers, such as divalproex. However, these predictors of acute response may not generalize to maintenance treatment. Lithium responders are more likely to have a strong family history of bipolar disorder, and concordant rather than discordant identical twins are more likely to respond to lithium. A family prospective study indicates that offspring of lithium responders are more likely to have a typical course with euphoric mania and less chronicity. Patients with comorbid disorders, such as substance abuse or anxiety disorders, are less likely to respond to lithium. Lithium responders may also be less likely to have good interepisode recovery than non-responders.

The Table immediately below demonstrates clinical predictors of mood stabilizer responses. For example, response to lithium treatment in bipolar disorder are associated with a positive family history.

Clinical Predictors of Mood Stabilizer Response

|  | Lithium | Depakote Carbamazepine | Lamotrigine |
| --- | --- | --- | --- |
| +Family History | + | − | ? |
| Mixed States | − | + | +? |
| Rapid Cycling | − | + | +? |
| Depression | + | − | ++ |

The distinct clinical profile of good lithium responders and the association with strong family history suggests that lithium responders may have a genetically distinct subform of bipolar illness. Turecki and colleagues have employed lithium responsive bipolar disorder as a phenotype for genetic linkage studies and identified a novel locus on 15q (Mapping susceptibility genes for bipolar disorder: a pharmacogenetic approach based on excellent response to lithium, Martina Ruzickova, Gustavo Turecki, Martin Alda. American Journal of Medical Genetics Part C: Seminars in Medical Genetics Volume 123C, Issue 1, pp. 18-25). These data indicate that a pharmacogenetic approach to lithium response might lead to the identification of genetic variants associated with response to specific medications.

A variety of signaling and biochemical pathways have been proposed for lithium's mechanism of action (Pharmacogenetics and bipolar disorder. Mamdani et al., 4(3):161-170, 2004). These provide numerous candidate genes to test for possible association with response. Prominent among these are signaling pathways involving inositol turnover. Inositol phosphatases (IMPA1, IMPA2, INPP1) are involved in recycling IP3 to inositol in the cell membrane. Lithium may dampen inositol signaling by depleting inositol through inhibition of these phosphatases. INPP1 polymorphisms have been associated with lithium response in a small sample. Lithium may also affect signaling via G proteins. G protein receptor kinase 3 (GRK3) is involved in homologous desensitization of G protein coupled receptors, which was previously reported to be a susceptibility gene for bipolar disorder. Brain derived neurotrophic factor (BDNF) and its receptor Trkb (NTRK2) are induced by lithium, implicating neurotrophic factors in lithium's mechanism of action. Glycogen synthase kinase 3 beta (GSK3B), a regulator of the Wnt signaling pathway involved in neuronal cell development, is inhibited by lithium (Stambolic V Curr Biol 7(3):196). Myristoylated alanine-rich C kinase substrate (MARCKS) is a protein kinase C target that is reduced by chronic lithium treatment. Furthermore, an insertion/deletion variant (5-HT-TLPR) in the promoter of the serotonin transporter gene (SLC6A4/5-HTT), extensively studied in both mood disorder and drug response, is also associated with lithium response in bipolar disorder.

In the context of this disclosure, the terms below shall be defined as follows unless otherwise indicated:

An allele is a particular form of a genetic locus, distinguished from other forms by its particular nucleotide sequence, or one of the alternative polymorphisms found at a polymorphic site.

A gene refers to a segment of genomic DNA that contains the coding sequence for a protein, wherein the segment may include promoters, exons, introns, and other untranslated regions that control expression.

A genotype is an unphased 5' to 3' sequence of nucleotide pair(s) found at a set of one or more polymorphic sites in a locus on a pair of homologous chromosomes in an individual. As used herein, genotype includes a full-genotype and/or a sub-genotype.

Genotyping is a process for determining a genotype of an individual.

A haplotype is a 5' to 3' sequence of nucleotides found at a set of one or more polymorphic sites in a locus on a single chromosome from a single individual.

Haplotype pair is two haplotypes found for a locus in a single individual.

Haplotyping is the process for determining one or more haplotypes in an individual and includes use of family pedigrees, molecular techniques and/or statistical inference.

A genetic locus refers to a location on a chromosome or DNA molecule corresponding to a gene or a physical or phenotypic feature, where physical features include polymorphic sites.

Polymorphic site (PS) a position on a chromosome or DNA molecule at which at least two alternative sequences are found in a population.

A polymorphism refers to the sequence variation observed in an individual at a polymorphic site. Polymorphisms include nucleotide substitutions, insertions, deletions and microsatellites and may, but need not, result in detectable differences in gene expression or protein function. A single nucleotide polymorphism (SNP) is a single change in the nucleotide variation at a polymorphic site.

An oligonucleotide probe or a primer refers to a nucleic acid molecule of between 8 and 2000 nucleotides in length, or is specified to be about 6 and 1000 nucleotides in length. More particularly, the length of these oligonucleotides can range from about 8, 10, 15, 20, or 30 to 100 nucleotides, but will typically be about 10 to 50 (e.g., 15 to 30 nucleotides). The appropriate length for oligonucleotides in assays of the invention under a particular set of conditions may be empirically determined by one of skill in the art.

Oligonucleotide primers and probes can be prepared by any suitable method, including, for example, cloning and restriction of appropriate sequences and direct chemical synthesis.

Oligonucleotide probes and primers can comprise nucleic acid analogs such as, for example peptide nucleic acids, locked nucleic acid (LNA) analogs, and morpholino analogs. The 3' end of the probe can be functionalized with a capture or detectable label to assist in detection of a polymorphism.

Any of the oligonucleotides or nucleic acid of the invention can be labeled by incorporating a detectable label measurable by spectroscopic, photochemical, biochemical, immunochemical, or chemical means. For example, such labels can comprise radioactive substances ($^{32}P$, $^{35}S$, $^{3}H$, $^{125}I$) fluorescent dyes (5-bromodesoxyuridin, fluorescein, acetylaminofluorene, digoxigenin), biotin, nanoparticles, and the like. Such oligonucleotides are typically labeled at their 3' and 5' ends.

A reference or control population refers to a group of subjects or individuals who are predicted to be representative of the genetic variation found in the general population. Typically, the reference population represents the genetic variation in the population at a certainty level of at least 85%, typically at least 90%, least 95% and but commonly at least 99%.

A subject comprises an individual (e.g., a mammalian subject or human) whose genotypes or haplotypes or response to treatment or disease state are to be determined.

A probe refers to a molecule which can detectably distinguish between target molecules differing in structure. Detection can be accomplished in a variety of different ways depending on the type of probe used and the type of target molecule. Thus, for example, detection may be based on discrimination of activity levels of the target molecule, but typically is based on detection of specific binding. Examples of such specific binding include antibody binding and nucleic acid probe hybridization. Thus, for example, probes can include enzyme substrates, antibodies and antibody fragments, and nucleic acid hybridization probes. Thus, in one embodiments, the detection of the presence or absence of the at least one variance involves contacting a target polymorphic site with a probe, typically an oligonucleotide probe, where the probe hybridizes with a form of the target nucleic acid containing a complementary base at the variance site as compared to hybridization to a form of the target nucleic acid having a non-complementary base at the variance site, where the hybridization is carried out under selective hybridization conditions. Such an oligonucleotide probe may span two or more variance sites. Unless otherwise specified, an oligonucleotide probe can include one or more nucleic acid analogs, labels or other substituents or moieties so long as the base-pairing function is retained.

The invention provides a number of polymorphisms useful for predicting a subject's response to lithium treatment. The SNPs identified herein can be used in combination with additional predictive tests including, but not limited to, additional SNPs, mutations, and clinical tests.

In one embodiment of the invention, an oligonucleotide probe comprises a sequence as set forth in the table below:

TABLE 1

| Gene | dbSNP id (rs#) | Celera id | Sequence |
|------|---------------|-----------|----------|
| GRK3 | rs133845 | hCV2190077 | TCTAACTCCTCAGAGAGCACGTAAA [A/C] CATGAATCTACCCT GTAGTTGCTGT (SEQ ID NO: 1, 2, respectively) |
| GRK3 | rs11913984 | hCV2190048 | TTCTCTTATTTGATGGAAATTTTAT [C/G] TTTTTACAACCCCA TTATCAGTTTG (SEQ ID NO: 3, 4, respectively) |
| NTRK2 | rs1187287 | | TAGGGACTTGCGTTGGTAATGAATA [C/T] CATGGTTTAGATGT TTATTGCTGTA (SEQ ID NO: 5, 6, respectively) |
| NTRK2 | rs1387923 | | TATATGGCCAAACCAAAGGTCAACA [C/T] TGAAAATAAAAGTC CTGAGACAGGG (SEQ ID NO: 7, 8, respectively) |
| NTRK2 | rs1565445 | | AAGCAGGCAAAGGTGTGGCTAAAAA [C/T] CACCTTCCAAGTAA TGAGGCAGTAC (SEQ ID NO: 9, 10, respectively) |

TABLE 1-continued

| Gene | dbSNP id (rs#) | Celera id | Sequence |
|---|---|---|---|
| NTRK2 | rs1187352 | | ACAGTGAGCAAGAGTCAGACAATTC [A/G] GGCATAGGCCCCTC TGCCACCTCAC (SEQ ID NO: 11, 12, respectively) |
| IMPA2 | rs971363 | | CGGCTGGACTTTATAAACTCTTCAC [A/C] CCCAAAACTCGAAT TTGGAGACGGA (SEQ ID NO: 13, 14, respectively) |
| IMPA1 | rs915 | | ATCACTCCCTACCTTGAAAACTTTA [C/T] AGAAGCATTTTTAA TTTTACAACAC (SEQ ID NO: 11, 12, respectively) |

Other polymorphism include INPP1 (rs2016037), NTRK2 (rs1619120), INPP1 (rs972691), IMPA2 (rs971362), and BDNF (rs2049045). For example, oligonucleotide probes of the invention comprise at least 8 nucleotides of SEQ ID NOs:1-15, and/or 16 containing the underlined sequence above and wherein the oligonucleotide specifically hybridizes to a polynucleotide sample from a subject comprising SEQ ID NO:1-16. In one aspect, an oligonucleotide probe of the invention comprises SEQ ID NO:1-15 or 16 having at least 8 nucleotide and containing nucleotides 25-27 (e.g., from about nucleotide 20 to nucleotide 30 of SEQ ID NO:1-15 or 16); and any of the foregoing sequences wherein T can be U; and complements of any of the foregoing.

As mentioned above, such probes can comprise nucleotide analogs useful for hybridization such as Locked Nucleic Acids (LNA). As described herein, such probes can be immobilized on a substrate such as a gene chip.

Any of the oligonucleotide primers and probes of the invention can be immobilized on a solid support. Solid supports are known to those skilled in the art and include the walls of wells of a reaction tray, test tubes, polystyrene beads, magnetic beads, nitrocellulose strips, membranes, microparticles such as latex particles, glass and the like. The solid support is not critical and can be selected by one skilled in the art. Thus, latex particles, microparticles, magnetic or nonmagnetic beads, membranes, plastic tubes, walls of microtiter wells, glass or silicon chips and the like are all suitable examples. Suitable methods for immobilizing oligonucleotides on a solid phase include ionic, hydrophobic, covalent interactions and the like. The solid support can be chosen for its intrinsic ability to attract and immobilize the capture reagent. The oligonucleotide probes or primers of the invention can be attached to or immobilized on a solid support individually or in groups of about 2-10,000 distinct oligonucleotides of the invention to a single solid support.

A substrate comprising a plurality of oligonucleotide primers or probes of the invention may be used either for detecting or amplifying targeted sequences in polymorphic region of NTRK2, GRK3 and/or IMPA1 or -2 genes based upon the polymorphic sequences above.

The oligonucleotide probes and primers of the invention can be attached in contiguous regions or at random locations on the solid support. Alternatively the oligonucleotides of the invention may be attached in an ordered array wherein each oligonucleotide is attached to a distinct region of the solid support which does not overlap with the attachment site of any other oligonucleotide. Typically, such oligonucleotide arrays are "addressable" such that distinct locations are recorded and can be accessed as part of an assay procedure. The knowledge of the location of oligonucleotides on an array make "addressable" arrays useful in hybridization assays. For example, the oligonucleotide probes can be used in an oligonucleotide chip such as those marketed by Affymetrix and described in U.S. Pat. No. 5,143,854; PCT publications WO 90/15070 and 92/10092, the disclosures of which are incorporated herein by reference. These arrays can be produced using mechanical synthesis methods or light directed synthesis methods which incorporate a combination of photolithographic methods and solid phase oligonucleotide synthesis.

The immobilization of arrays of oligonucleotides on solid supports has been rendered possible by the development of a technology generally referred to as "Very Large Scale Immobilized Polymer Synthesis" in which probes are immobilized in a high density array on a solid surface of a chip (see, e.g., U.S. Pat. Nos. 5,143,854; and 5,412,087 and in PCT Publications WO 90/15070, WO 92/10092 and WO 95/11995, each of which are incorporated herein by reference), which describe methods for forming oligonucleotide arrays through techniques such as light-directed synthesis techniques.

In another embodiment, one or more additional polymorphic genes may be analyzed. For example, in addition to NTRK2, GRK3 and IMPA1 and -2, polymorphic detection of ADRBK2, BNDF, GSK3B, INPP1, MARCKS, and/or NR1I2 gene(s) may be performed.

In another aspect, an array of oligonucleotides complementary to subsequences of the target gene is used to determine the identity of the target, measure its amount, and detect differences between the target and a reference wild-type sequence. In one such design, termed 4L tiled array, is implemented a set of four probes (A, C, G, T), typically 15-nucleotide oligomers in length. In each set of four probes, the perfect complement will hybridize more strongly than mismatched probes. Consequently, hybridization signals of the 15-mer probe set tiled array are perturbed by a single base change in the target sequence resulting in a characteristic loss of signal.

Primers useful in the invention include oligonucleotides comprising sequence that flank the underlined sequence above or that comprise a sequence that contains the underlined nucleotide at the 3' end, thus, for example, preventing primer extension in PCR reactions thus providing a detectable event.

The invention further contemplates, antibodies capable of specifically binding to a variant polypeptide (e.g., a variant GRK3, NTRK2, IMPA1 or -2, polypeptide) encoded in proper frame, based upon transcriptional and translational starts, of the above-identified oligonucleotide sequences (e.g., SEQ ID NOs: 1-16). The invention thus includes isolated, purified, and recombinant polypeptides comprising a contiguous span of at least 4 amino acids, typically at least 6, more commonly at least 8 to 10 amino acids encoded by SEQ ID NOs:1-15 or 16. The contiguous stretch of amino acids comprises the site of a variation (e.g., the underlined nucleotide above).

In one embodiment of the invention, polynucleotides (e.g., DNA) are obtained from a subject's blood or saliva (or other sample useful for obtaining a polynucleotide sample). The subject's sample is then used to test for a variant (e.g., rs1387923) associated with bipolar disease and indicative of lithium response.

In one aspect, the invention measures a variant in the gene NTRK2. If the subject has primarily a lifetime history of euphoric mania, then this variant will predict whether the subject has, for example, a 34, 62, or 83% probability of responding well to lithium depending on whether they have a minor homozygousity, heterozygousity or major homozygousity genotype, respectively, for the variant.

Methods for diagnostic tests are well known in the art. Generally, the diagnostic test of the invention involves determining whether an individual has a variance or variant form of a gene that is involved in the action of the drug (e.g., lithium) or other treatment or effects of such treatment. Such a variance or variant form of the gene are identified herein and have been identified within the population and are known to be present at a certain frequency. In an exemplary method, the diagnostic test involves amplifying a segment of DNA or RNA (generally after converting the RNA to cDNA) spanning one or more polymorphic regions in a gene (e.g., see Table above). In many cases, the diagnostic test is performed by amplifying a segment of DNA or RNA (cDNA) spanning a polymorphism, or even spanning more than one polymorphisms in the gene (e.g., an NTRK2, GRK3, and/or IMPA1-2 gene).

Diagnostic tests useful for practicing the invention typically belong to two types: genotyping tests and haplotyping tests. A genotyping test simply provides the status of a variance or variances in a subject. For example suppose nucleotide 150 of hypothetical gene X on an autosomal chromosome is an adenine (A) or a guanine (G) base. The possible genotypes in any individual are AA, AG or GG at nucleotide 150 of gene X.

In a haplotyping test there is at least one additional variance in gene X, say at nucleotide 810, which varies in the population as cytosine (C) or thymine (T). Thus a particular copy of gene X may have any of the following combinations of nucleotides at positions 150 and 810: 150A-810C, 150A-810T, 150G-810C or 150G-810T. Each of the four possibilities is a unique haplotype. If the two nucleotides interact in either RNA or protein, then knowing the haplotype can be important. The point of a haplotyping test is to determine the haplotypes present in a DNA or CDNA sample (e.g. from a subject).

Based on the identification of variances or variant forms of a gene, a diagnostic test utilizing methods known in the art can be used to determine whether a particular form of the gene, containing specific variances or haplotypes, or combinations of variances and haplotypes, is present in at least one copy, or more than one copy in a subject. Such tests are performed using DNA or RNA samples collected from blood, cells, tissue scrapings or other cellular materials, and can be performed by a variety of methods including, but not limited to, hybridization with allele-specific probes, enzymatic mutation detection, chemical cleavage of mismatches, mass spectrometry or DNA sequencing, including minisequencing. Diagnostic tests may involve a panel of variances from one or more genes, often on a solid support, which enables the simultaneous determination of more than one variance in one or more genes.

The invention provides polymorphic sequences identified above that may be determined using diagnostic tests. As described herein, such a variance-based diagnostic test can be used to determine whether or not to administer a specific drug or other treatment to a subject for treatment of a disease or condition.

Cloning and sequencing of the NTRK2, GRK3, IMPA1 and/or -2 genes can serve to detect variants useful in predicting a lithium response. Commonly used sequencing techniques can be carried out with commercially available automated sequencers, for example, utilizing fluorescently labeled primers. Other methods of sequence are known in the art.

The target region(s) containing the polymorphism of interest may be amplified using any oligonucleotide-directed amplification method including, but not limited to, polymerase chain reaction (PCR) (U.S. Pat. No. 4,965,188), ligase chain reaction (LCR) (Barany et al., Proc. Natl. Acad. Sci. USA 88:189-93 (1991); WO 90/01069), and oligonucleotide ligation assay (OLA) (Landegren et al., Science 241:1077-80 (1988)). Other known nucleic acid amplification procedures may be used to amplify the target region(s) including transcription-based amplification systems (U.S. Pat. No. 5,130, 238; European Patent No. EP 329,822; U.S. Pat. No. 5,169, 766; WO 89/06700) and isothermal methods (Walker et al., Proc. Natl. Acad. Sci. USA 89:392-6 (1992)).

Ligase Chain Reaction (LCR) techniques can be used. LCR occurs only when the oligonucleotides are correctly base-paired. The Ligase Chain Reaction (LCR), which utilizes the thermostable Taq ligase for ligation amplification, is useful for interrogating loci of a gene (e.g., SEQ ID NO:1-16). A method of DNA amplification similar to PCR, LCR differs from PCR because it amplifies the probe molecule rather than producing amplicon through polymerization of nucleotides. Two probes are used per each DNA strand and are ligated together to form a single probe. LCR uses both a DNA polymerase enzyme and a DNA ligase enzyme to drive the reaction. Like PCR, LCR requires a thermal cycler to drive the reaction and each cycle results in a doubling of the target nucleic acid molecule. LCR can have greater specificity than PCR. The elevated reaction temperatures permits the ligation reaction to be conducted with high stringency. Where a mismatch occurs, ligation cannot be accomplished. For example, a primer is synthesized in two fragments and annealed to the template with possible mutation at the boundary of the two primer fragments (i.e., the underlined nucleotide above would be found at the 5' or 3' end of the oligonucleotide). A ligase ligates the two primers if they match exactly to the template sequence.

In one embodiment, the two hybridization probes are designed each with a target specific portion. The first hybridization probe is designed to be substantially complementary to a first target domain of a target polynucleotide (e.g., a polynucleotide fragment) and the second hybridization probe is substantially complementary to a second target domain of a target polynucleotide (e.g., a polynucleotide fragment). In general, each target specific sequence of a hybridization probe is at least about 5 nucleotides long, with sequences of about 15 to 30 being typical and 20 being especially common. In one embodiment, the first and second target domains are directly adjacent, e.g., they have no intervening nucleotides. In this embodiment, at least a first hybridization probe is hybridized to the first target domain and a second hybridization probe is hybridized to the second target domain. If perfect complementarity exists at the junction, a ligation structure is formed such that the two probes can be ligated together to form a ligated probe. If this complementarity does not exist (due to mismatch based upon a variant), no ligation structure is formed and the probes are not ligated together to an appreciable degree. This may be done using heat cycling, to allow the ligated probe to be denatured off the target polynucleotide such that it may serve as a template for further reactions. The method may also be done using three hybridization probes or hybridization probes that are separated by one or more nucleotides, if dNTPs and a polymerase are added (this is sometimes referred to as "Genetic Bit" analysis).

Analysis of point mutations in DNA can also be carried out by using the polymerase chain reaction (PCR) and variations thereof. Mismatches can be detected by competitive oligonucleotide priming under hybridization conditions where binding of the perfectly matched primer is favored. In the amplification refractory mutation system technique (ARMS), primers are designed to have perfect matches or mismatches with target sequences either internal or at the 3' residue (Newton et al., Nucl. Acids. Res. 17:2503-2516 (1989)). Under appropriate conditions, only the perfectly annealed oligonucleotide functions as a primer for the PCR reaction, thus providing a method of discrimination between normal and variant sequences.

Single nucleotide primer-guided extension assays can also be used, where the specific incorporation of the correct base is provided by the fidelity of a DNA polymerase. Detecting the nucleotide or nucleotide pair at a PS of interest may also be determined using a mismatch detection technique including, but not limited to, the RNase protection method using riboprobes (Winter et al., Proc. Natl. Acad. Sci. USA 82:7575 (1985); Meyers et al., Science 230:1242 (1985)) and proteins which recognize nucleotide mismatches, such as the $E.\ coli$ mutS protein (Modrich, Ann. Rev. Genet. 25:229-53 (1991)). Alternatively, variant alleles can be identified by single strand conformation polymorphism (SSCP) analysis (Orita et al., Genomics 5:874-9 (1989); Humphries et al., in MOLECULAR DIAGNOSIS OF GENETIC DISEASES, Elles, ed., pp. 321-340, 1996) or denaturing gradient gel electrophoresis (DGGE) (Wartell et al., Nucl. Acids Res. 18:2699-706 (1990); Sheffield et al., Proc. Natl. Acad. Sci. USA 86:232-6 (1989)).

Hybridization techniques can also be used to identify the polymorphisms of the invention and thereby determine a predictive response to lithium. In this aspect, polymorphism(s) are identified based upon the higher thermal stability of a perfectly matched probe compared to the mismatched probe. The hybridization reactions may be carried out in a solid support (e.g., membrane) format, in which the target nucleic acids are immobilized on nitrocellulose or nylon membranes and probed with oligonucleotide probes of the invention. Any of the known hybridization formats may be used, including Southern blots, slot blots, "reverse" dot blots, solution hybridization, solid support based sandwich hybridization, bead-based, silicon chip-based and microtiter well-based hybridization formats.

In one aspect, a sandwich hybridization assay comprises separating the variant and wild-type target nucleic acids in a sample using a common capture oligonucleotide immobilized on a solid support and then contact with specific probes useful for detecting the variant and wild-type nucleic acids. The oligonucleotide probes are typically tagged with a detectable label.

A polymorphism in a target region of a gene may be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one PS may be detected at once using a set of allele-specific oligonucleotides or oligonucleotide pairs. Typically, the members of the set have melting temperatures within 5° C., and more typically within 2° C., of each other when hybridizing to each of the polymorphic sites being detected.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The detectable label may be a radioactive label or may be a luminescent, fluorescent of enzyme label. Indirect detection processes typically comprise probes covalently labeled with a hapten or ligand such as digoxigenin (DIG) or biotin. Following the hybridization step, the target-probe duplex is detected by an antibody- or streptavidin-enzyme complex. Enzymes commonly used in DNA diagnostics are horseradish peroxidase and alkaline phosphatase. Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes.

Label detection will be based upon the type of label used in the particular assay. Such detection methods are known in the art. For example, radioisotope detection can be performed by autoradiography, scintillation counting or phosphor imaging. For hapten or biotin labels, detection is with an antibody or streptavidin bound to a reporter enzyme such as horseradish peroxidase or alkaline phosphatase, which is then detected by enzymatic means. For fluorophor or lanthanide-chelate labels, fluorescent signals may be measured with spectrofluorimeters with or without time-resolved mode or using automated microtitre plate readers. With enzyme labels, detection is by color or dye deposition (p-nitropheny phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g., 4-methyl umbelliferyl phosphate for alkaline phosphatase) or chemiluminescence (the alkaline phosphatase dioxetane substrates LumiPhos 530 from Lumigen Inc., Detroit Mich. or AMPPD and CSPD from Tropix, Inc.). Chemiluminescent detection may be carried out with X-ray or polaroid film or by using single photon counting luminometers.

In one aspect, the invention provides oligonucleotides and methods to genotype one or more biallelic markers of the invention by performing a microsequencing assay. It will be appreciated any primer having a 3' end immediately adjacent to a polymorphic nucleotide may be used. Similarly, it will be appreciated that microsequencing analysis may be performed for any biallelic marker or any combination of biallelic markers of the invention. One aspect of the invention is a solid support which includes one or more microsequencing primers for the SNPs listed herein, or fragments comprising at least 8, at least 12, at least 15, or at least 20 consecutive nucleotides of SEQ ID NO:1-16 and having a 3' terminus immediately upstream of the polymorphism.

Hybridization assays based on oligonucleotide arrays rely on the differences in hybridization stability of short oligonucleotides to perfectly matched and mismatched target variants. Efficient access to polymorphism information is obtained through a basic structure comprising high-density arrays of oligonucleotide probes attached to a solid support (the chip) at selected positions. Each DNA chip can contain thousands to millions of individual synthetic DNA probes arranged in a grid-like pattern and miniaturized to the size of a dime or smaller. Such a chip may comprise oligonucleotides representative of both the wild-type and variant sequences oligonucleotides of the invention can be designed to specifically hybridize to a target region of a polynucleotide containing a desired locus. As used herein, specific hybridization means the oligonucleotide forms an anti-parallel double-stranded structure with the target region under certain hybridizing conditions, while failing to form such a structure when incubated with another region in the polynucleotide or with a polynucleotide lacking the desired locus under the same hybridizing conditions. Typically, the oligonucleotide specifically hybridizes to the target region under conventional high stringency conditions.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, in Sambrook et al., Molecular Cloning, A Laboratory Manual, 2nd ed., Cold Spring Harbor Press, Cold Spring Harbor, N.Y. (1989), and in Haymes et al., Nucleic Acid Hybridization, A Practical Approach, IRL Press, Washington, D.C. (1985). While perfectly complementary oligonucleotides are used in most assays for detecting polymorphisms, departures from complete complementarity are contemplated where such departures do not prevent the molecule from specifically hybridizing to the target region. For example, an oligonucleotide primer may have a non-complementary fragment at its 5' or 3' end, with the remainder of the primer being complementary to the target region. Those of skill in the art are familiar with parameters that affect hybridization; such as temperature, probe or primer length and composition, buffer composition and salt concentration and can readily adjust these parameters to achieve specific hybridization of a nucleic acid to a target sequence.

A variety of hybridization conditions may be used in the disclosure, including high, moderate and low stringency conditions; see for example Maniatis et al., Molecular Cloning: A Laboratory Manual, 2d Edition, 1989, and Short Protocols in Molecular Biology, ed. Ausubel, et al., hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the polyadenylated mRNA target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of helix destabilizing agents such as formamide. The hybridization conditions may also vary when a non-ionic backbone, i.e., PNA is used, as is known in the art. In addition, cross-linking agents may be added after target binding to cross-link, i.e., covalently attach, the two strands of the hybridization complex.

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524. Related methods are disclosed in WO 91/02087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798. Another primer extension method is allele-specific PCR (Ruano et al., 1989, supra; Ruano et al., 1991, supra; WO 93/22456; Turki et al., J. Clin. Invest. 95:1635-41 (1995)). In addition, multiple PSs may be investigated by simultaneously amplifying multiple regions of the nucleic acid using sets of allele-specific primers as described in WO 89/10414.

For example, the genotype or haplotype for the NTRK2 gene of an subject may also be determined by hybridization of a nucleic acid sample containing one or both copies of the gene, mRNA, cDNA or fragment(s) thereof, to nucleic acid arrays and subarrays such as described in WO 95/11995. The arrays would contain a battery of allele-specific oligonucleotides representing each of the PSs to be included in the genotype or haplotype.

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, the disclosure of which is incorporated herein by reference in its entirety, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip. For genotyping biallelic markers, the microfluidic system may integrate nucleic acid amplification, microsequencing, capillary electrophoresis and a detection method such as laser-induced fluorescence detection.

The invention also contemplates the use of immunoassay techniques for measurement of the polymorphisms identified herein for prediction of lithium response. For example, point mutations (as identified in SEQ ID NO:1-16) may alter the structure of the proteins for which these gene encode. These altered polypeptides (e.g., NTRK2, GRK3, IMPA1 and -2 polypeptides) can be isolated and used to prepare antisera and monoclonal antibodies that specifically detect the mutated gene products and not those of non-mutated or wild-type gene products. Mutated gene products also can be used to immunize animals for the production of polyclonal antibodies. Recombinantly produced peptides can also be used to generate antibodies. For example, a recombinantly produced fragment of a variant polypeptide can be injected into a mouse along with an adjuvant so as to generate an immune response. Murine immunoglobulins which bind the recombinant fragment with a binding affinity of at least $1\times10^7$ $M^{-1}$ can be harvested from the immunized mouse as an antiserum, and may be further purified by affinity chromatography or other means. Additionally, spleen cells are harvested from the mouse and fused to myeloma cells to produce a bank of antibody-secreting hybridoma cells. The bank of hybridomas can be screened for clones that secrete immunoglobulins which bind the recombinantly produced fragment with an affinity of at least $1\times10^6$ $M^{-1}$. More specifically, immunoglobulins that selectively bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Polynucleotides capable of expressing the desired variant polypeptides can be generated using techniques skilled in the art based upon the identified polymorphisms herein. Such polynucleotides can be expressed in hosts, wherein the polynucleotide is operably linked to (i.e., positioned to ensure the functioning of) an expression control sequence. Expression vectors are typically replicable in the host organisms either as episomes or as an integral part of the host chromosome. Expression vectors can contain selection markers (e.g., markers based on tetracyclin resistance or hygromycin resistance) to permit detection and/or selection of those cells transformed with the desired polynucleotide.

Polynucleotides encoding a variant polypeptide may include sequences that facilitate transcription and translation of the coding sequences such that the encoded polypeptide product is produced. Construction of such polynucleotides is known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Prokaryotes can be used as host cells for the expression of a variant polypeptides, such techniques are known in the art. Other microbes, such as yeast, may also be used for expression. In addition to microorganisms, mammalian tissue cell culture may also be used to express and produce polypeptides of the invention. Eukaryotic cells useful in the methods of the invention include the CHO cell lines, various COS cell lines, HeLa cells, myeloma cell lines, Jurkat cells, and so forth. Expression vectors for these cells can include expression control sequences, such as an origin of replication, a promoter, an enhancer, an necessary information processing sites, such as ribosome binding sites, RNA splice sites, polyadenylation sites, and transcriptional terminator sequences.

Linkage disequilibrium is the non-random association of alleles at two or more loci and represents a powerful tool for mapping genes involved in disease traits. Biallelic markers, because they are densely spaced in the human genome and can be genotyped in more numerous numbers than other types of genetic markers, are particularly useful in genetic analysis based on linkage disequilibrium.

Briefly, when a mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation: one finds the disease mutation only in the presence of a specific set of marker alleles. Through subsequent generations recombinations occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination, "ancestral" haplotypes and linkage disequilibrium between marker alleles at different loci can be tracked not only through pedigrees but also through populations. Linkage disequilibrium is usually seen as an association between one specific allele at one locus and another specific allele at a second locus.

The pattern or curve of disequilibrium between disease and marker loci is expected to exhibit a maximum that occurs at the locus. Consequently, the amount of linkage disequilibrium between an allele and closely linked genetic markers may yield valuable information regarding the location of a disease gene. For fine-scale mapping of a disease locus, it is useful to have some knowledge of the patterns of linkage disequilibrium that exist between markers in the studied region.

A number of methods can be used to calculate linkage disequilibrium between any two genetic positions, in practice linkage disequilibrium is measured by applying a statistical association test to haplotype data taken from a population.

While direct haplotyping of both copies of the gene can be performed with each copy of the gene analyzed independently, it is also envisioned that direct haplotyping could be performed simultaneously if the two copies are labeled with different tags, or are otherwise separately distinguishable or identifiable. For example, if first and second copies of the gene are labeled with different first and second fluorescent dyes, respectively, and an allele-specific oligonucleotide labeled with yet a third different fluorescent dye is used to assay the polymorphism(s), then detecting a combination of the first and third dyes would identify the polymorphism in the first gene copy while detecting a combination of the second and third dyes would identify the polymorphism in the second gene copy.

In both the direct and indirect haplotyping methods, the identity of a nucleotide (or nucleotide pair) at a PS(s) in the amplified target region may be determined by sequencing the amplified region(s) using conventional methods. If both copies of the gene are represented in the amplified target, it will be readily appreciated by the skilled artisan that only one nucleotide will be detected at a PS in individuals who are homozygous at that site, while two different nucleotides will be detected if the individual is heterozygous for that site. The polymorphism may be identified directly, known as positive-type identification, or by inference, referred to as negative-type identification. For example, where a polymorphism is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

Once a first biallelic marker has been identified in a genomic region of interest, the practitioner of ordinary skill in the art, using the teachings of the invention, can easily identify additional biallelic markers in linkage disequilibrium with this first marker. As mentioned before, any marker in linkage disequilibrium with a first marker associated with a trait will be associated with the trait. Therefore, once an association has been demonstrated between a given biallelic marker and a trait, the discovery of additional biallelic markers associated with this trait is of interest in order to increase the density of biallelic markers in this particular region. The causal gene or mutation will be found in the vicinity of the marker or set of markers showing the highest correlation with the trait.

Identification of additional markers in linkage disequilibrium with a given marker involves: (a) amplifying a genomic fragment comprising a first biallelic marker from a plurality of individuals; (b) identifying of second biallelic markers in the genomic region harboring said first biallelic marker; (c) conducting a linkage disequilibrium analysis between said first biallelic marker and second biallelic markers; and (d) selecting said second biallelic markers as being in linkage disequilibrium with said first marker. Subcombinations comprising steps (b) and (c) are also contemplated.

The invention provides assays which may be used to identify subjects that response to a particular therapeutic treatment. For example, in one aspect, the assays of the invention identify one or more SNPs that have been associated with a clinical manifestation or response to lithium. Thus, identifying such SNPs in a subject can provide information indicative of that subject's response to, for example, lithium.

The present invention also provides cell and animal, including primate and mouse, models of lithium responsiveness. In one aspect, provided are non-cell based, cell based and animal based assays for the identification of compounds that affect NTRK2, GRK3, IMPA1 and/or -2 activity. The invention has identified polymorphisms associated with lithium response. Accordingly, genetically engineered organisms (including non-human transgenic animals) comprising an homolog or variant of the invention can be used to assess responsiveness of the organism to compounds useful in treating mental disorders.

In one aspect, cell based assays using recombinant or non-recombinant cells may be used to identify compounds which modulate NTRK2, GRK3, IMPA-1 and/or -2 expression or activity. A cell based assay of the invention encompasses a method for identifying a test compound for the treatment of schizophrenia or bipolar disorder comprising (a) exposing a cell to a test compound at a concentration and time sufficient to ameliorate an endpoint related to schizophrenia or bipolar disorder, and (b) determining the level of NTRK2, GRK3, IMPA-1 and/or -2 activity in a cell. Such techniques may include measuring other activities including, for example, ADRBK2, BNDF, GSK3B, INPP1, MARCKS, and/or NR1I2 activity. Such measurement can include measuring, for example, transcription level, polypeptide expression, localization or activity. Typically, the test compound is a compound capable of or suspected to be capable of ameliorating a symptom of schizophrenia, bipolar disorder or a related disorder.

In another embodiment, a NTRK2, GRK3, IMPA-1 and/or -2 polynucleotide, or fragments thereof, is cloned into expression vectors. The polynucleotide or fragment is then expressed the expression product purified by size, charge, immunochromatography or other techniques familiar to those skilled in the art. Following purification, the expression product(s) are labeled using techniques known to those skilled in the art. The labeled proteins are incubated with cells or cell lines derived from a variety of organs or tissues to allow the proteins to bind to any receptor present on the cell surface. Following the incubation, the cells are washed to remove non-specifically bound protein. The labeled proteins are detected. A test compound binding may be analyzed by conducting a competition analysis in which various amounts of a test compound are incubated along with the labeled protein. The amount of labeled protein bound to the cell surface decreases as the amount of competitive unlabeled test compound increases.

Non-human animal-based assays may also be used to identify compounds which modulate NTRK2, GRK3, IMPA-1 and/or IMPA-2 activity. Thus, the invention comprises treating an animal comprising a homolog or variant comprising SEQ ID NO:1-15 and/or 16 with a test compound. In one aspect, an animal-based assay of the invention encompasses a method for identifying a test compound for the treatment of mood disorder comprising (a) exposing an animal to a test compound at a concentration and time sufficient to ameliorate an endpoint related to a mood disorder, and (b) determining the level of NTRK2, GRK3, IMPA-1 and/or IMPA-2 activity in an animal. In one aspect, the animal is a primate, a non-human primate, a mammal, or a mouse.

Any suitable test compound may be used with the screening methods of the invention. Examples of compounds that may be screened by the methods of the invention include small organic or inorganic molecules, nucleic acids (e.g., ribozymes, antisense molecules), including polynucleotides from random and directed polynucleotide libraries, peptides, including peptides derived from random and directed peptide libraries, soluble peptides, fusion peptides, and phosphopeptides, antibodies including polyclonal, monoclonal, chimeric, humanized, and anti-idiotypic antibodies, and single chain antibodies, FAb, F(ab')$_2$ and FAb expression library fragments, and epitope-binding fragments thereof. In certain aspects, a compound capable of ameliorating or exacerbating a symptom or endpoint of schizophrenia, bipolar disorder or a related disorder may include, by way of example, antipsychotic drugs in general, neuroleptics, atypical neuroleptics, antidepressants, anti-anxiety drugs, noradrenergic agonists and antagonists, dopaminergic agonists and antagonists, serotonin reuptake inhibitors, benzodiazepines.

In further methods, peptides, drugs, fatty acids, lipoproteins, or small molecules which interact with the NTRK2, GRK3, IMPA-1 and/or IMPA-2 protein, or a fragment comprising a contiguous span of at least 4 amino acids, at least 6 amino acids, or typically at least 8 to 10 amino acids or more of sequences corresponding to the SNPs of SEQ ID NO:1-15 and/or 16. The molecule to be tested for binding is labeled with a detectable label, such as a fluorescent, radioactive, or enzymatic tag and placed in contact with immobilized NTRK2, GRK3, IMPA-1 and/or IMPA-2 protein or a variant thereof under conditions which permit specific binding to occur. After removal of non-specifically bound molecules, bound molecules are detected using appropriate means.

In one embodiment, the invention provides a kit useful for identifying polymorphisms associated or predictive of lithium response. For example, the kit of the invention can comprise a of one or more oligonucleotides designed for identifying both alleles at each PS in the set of one or more PSs. In another embodiment, the kit further comprises a manual with instructions for (a) performing one or more reactions on a human nucleic acid sample to identify the allele or alleles present in the subject at each PS in the set of one or more PSs.

The oligonucleotides in a kit of the invention may also be immobilized on or synthesized on a solid surface such as a microchip, bead, or glass slide (see, e.g., WO 98/20020 and WO 98/20019). Such immobilized oligonucleotides may be used in a variety of polymorphism detection assays, including but not limited to probe hybridization and polymerase extension assays. Immobilized oligonucleotides useful in practicing the invention may comprise an ordered array of oligonucleotides designed to rapidly screen a nucleic acid sample for polymorphisms in multiple genes at the same time.

Kits of the invention may also contain other components such as hybridization buffer (e.g., where the oligonucleotides are to be used as allele-specific probes) or dideoxynucleotide triphosphates (ddNTPs; e.g., where the alleles at the polymorphic sites are to be detected by primer extension). In a one embodiment, the set of oligonucleotides consists of primer-extension oligonucleotides. The kit may also contain a polymerase and a reaction buffer optimized for primer-extension mediated by the polymerase. Preferred kits may also include detection reagents, such as biotin- or fluorescent-tagged oligonucleotides or ddNTPs and/or an enzyme-labeled antibody and one or more substrates that generate a detectable signal when acted on by the enzyme. It will be understood by the skilled artisan that the set of oligonucleotides and reagents for performing the genotyping or haplotyping assay will be provided in separate receptacles placed in the container if appropriate to preserve biological or chemical activity and enable proper use in the assay.

It is also contemplated that the above described methods and compositions of the invention may be utilized in combination with identifying genotype(s) and/or haplotype(s) for other genomic regions.

Nucleic acid samples, for example for use in variance identification, can be obtained from a variety of sources as known to those skilled in the art, or can be obtained from genomic or cDNA sources by known methods.

EXAMPLES

In the invention, 184 subjects with bipolar disorder, 92 who showed good lithium response and 92 who showed poor or partial response were analyzed. Eighty-nine genetic markers in nine candidate genes were genotyped for association with lithium response. The invention identifies SNPs in the NTRK2 and GRK3 genes that are associated with lithium response in subjects with euphoric and dysphoric manic states, respectively.

Four hundred subjects with bipolar disorder were screened for previous treatment response to lithium. These subjects were largely ascertained as probands of families for genetic linkage studies of bipolar disorder; hence, most were selected for having a family history of mood disorders. All subjects were Caucasians of European ancestry in order to reduce confounds related to population stratification. Some subjects were also specifically recruited for having a history of lithium treatment. Subjects were recruited from a variety of outpatient sources. All subjects provided written informed consent for the research.

Subjects were interviewed using one of several standardized instruments: the Structured Clinical Interview for DSM-III-R (SCID), the SCID for DSM-IV, or the Diagnostic Interview for Genetic Studies (DIGS) 31; 32. All interviewers for the study underwent a training course. Diagnostic reliability was tested regularly and was consistently high. Information was also collected from medical records and other family informants. The lifechart method 33 was used to identify mood episodes and medication trials. The interview instruments were modified so as to obtain additional information about bipolar disorder. In each mania or depression, symptoms of the opposite state were elicited in order to assess mixed states. A detailed review was also added regarding medication trials and responses that detailed the dates of the trials and the subject's judgment of response for each trial. These data were reviewed by a panel of experienced clinicians in order to determine the best estimate diagnosis and overall lifetime therapeutic response to lithium. The reviewing clinicians were blind to genotype.

Multiple trials of lithium treatment were reviewed, where available, in order to assess reduction of symptoms and reduction of episode frequency with maintenance treatment. For a lithium trial to be rated, it had to meet the following criteria:

1. Treatment was conducted with lithium alone for at least 3 months. Benzodiazepines and medications without known psychotropic effect for medical conditions were permitted. Trials with concurrent treatment with other mood stabilizers, antidepressant or antipsychotic treatment were excluded. Trials were also excluded if confounded with concurrent drug or alcohol dependence. 2. Lithium was added to an unsuccessful medication regimen. Trials were rated where a medication regimen had been employed without change for 3 months with no or only partial benefit and lithium was added for at least three months without other change in medications. The medication trial was rated based on the change resulting from augmentation with lithium.

Where subjects had clear trials of lithium monotherapy, these were used exclusively in order to assess response. All rated lithium trials were then considered together over the life course in order to rate overall lifetime response to lithium. Periods of time not on lithium after onset of illness, were compared to rated trials of lithium for episode frequency and overall symptom severity. Relapse prevention over the lifetime was the primary effect that was rated. However, some more ill patients had few or no periods of remission, for such patients reduction of overall symptoms was rated. Clinicians rated response in a semi-quantitative fashion as "good" (meaning >50% reduction of symptoms and episodes), "partial" (between 25-50% reduction of symptoms), or "poor" (<25% reduction of symptoms).

Approximately 75% of all subjects screened had a history of prior lithium treatment and at least one ratable lithium trial. This rate was elevated by the emphasis on lithium use in certain clinics and specific recruitment of some subjects for past lithium treatment with clean episodes. To optimized statistical power, an equal number of responders and non-responders were included in the analysis. Approximately, two thirds of ratable subjects were "good" lithium responders. Recruitment was therefore limited by the number of non-responders. Ninety-two responders (good) and 92 non-responders (partial or poor) ultimately met criteria for inclusion.

These data also were used to assess, in similar fashion, several other clinical features reported to be relevant to lithium response. Bipolar II was defined as meeting hypomania for at least two days instead of the four required by DSM-IV. Dysphoric mania was defined as having irritable mood and at least one other symptom of depression during at least one manic or mixed episode. Rapid cycling was defined, as in DSM-IV, as having four or more episodes per year with this frequency of cycling being characteristic of their illness.

Nine candidate genes were selected based on their association with lithium response or mechanism of action. For three of the genes (GRK3, GSK3B, and SLC6A4), a few selected genetic variants, previously shown to be associated with disease or treatment response, were genotyped. In the case of SLC6A4, this involved one repeat polymorphism in the upstream region (5-HTTLPR). For the remaining six genes, SNPs were selected from databases for informativeness and even distribution across the gene: SNPper (snpper.chip.org), dbSNP, or SNPbrowser (ABI). SNPs were selected for higher minor allele frequency and to achieve an approximate 10-20 kb density in each gene. Little data from the HapMap project was available at the time of SNP selection to guide this selection.

Blood was obtained from each subject and used to create immortalized lymphoblastoid cell lines. DNA was prepared from these cell lines using a standard phenol/chloroform extraction method. SNP genotyping was conducted using the ABI Taqman method 34. Primers were selected from the ABI web site ("on-demand") or custom designed by ABI from sequence using minor groove binding protein technology. Primers, 25 ng of DNA, probes, and master mix were included in 20-μl reactions. The 5-HTTLPR repeat polymorphism was assayed by PCR amplification using fluorescent primers, followed by electrophoretic separation on an ABI 3730.

Using $\chi 2$ analysis, three sets of tests for association were performed sequentially: 1) clinical characteristics, 2) stratified tests for a genotype "dose" response trend, 3) stratified tests for a dominant allelic effect. The outcome measure was defined as either positive or negative lithium treatment response, where the non-response set comprised those subjects with either poor or partial lithium response. The genetic marker $\chi 2$ tests were stratified to prevent spurious genotype associations from underlying significant clinical characteristics. The stratifying factor was the presence of either the dysphoric mania or rapid cycling subtypes, yielding a $\chi 2$ test as the sum of the two strata results. Family wise error rate (FWER) (p*-value) and false discovery rate (FDR) (q-value) measures were used to adjust for multiple comparisons accumulating over the three sets of association tests.

Non-polymorphic SNPs were removed from analysis. SNP markers were assessed for Hardy-Weinberg disequilibrium (HWD) by $\chi 2$ analysis, and those with extreme HWD ($\chi 2 > 6.6$) were removed, as they were likely the result of genotyping errors 35. $\chi 2$ tests were conducted only for genetic markers having contingency tables with cell frequencies of greater than six after stratification. The genotype "dose" response test was the $\chi 2$ test for trend in proportion, weighting genotype frequency. For those SNPs with insufficient cell frequencies for the genotype trend test, alternative coding schemes were employed to test for a dominant allelic effect and increase cell frequencies: (a) (nn, nN, NN)=(1, 1, 0, assuming that allele "n" was dominant; (b) (nn, nN, NN)=(0, 1, 1), assuming that allele "N" was dominant.

The FDR q-values were computed from the set of p-values, using the q-value package in the R statistical package with the "smoother" and "robust" options set. The FWER global permutation and Bonferroni methods were also applied. For the permutation method, adjusted global FWER p*-values were computed for all accumulated $\chi 2$ association tests. A null hypothesis distribution was constructed for each of the association tests, using 10,000 samples obtained by permuting the outcome label by bootstrap sampling with replacement. The global null hypothesis distribution, accounting for the interdependent genetic and clinical data structure, was formed from the composite of these samples and used to directly compute global p*-values. Additionally, due to its common use, the Bonferroni method was used to compute $p_b$*-values for reference. The multiple test correction was applied three times, once following the generation of each association test data (clinical characteristics, genotype trends, and dominant effects), accounting for all tests conducted through the current test set, but not for those tests not yet conducted.

After association testing, the significance of the interaction was assessed with log-linear analysis, and the contribution of the identified genetic markers to the lithium response above that of the clinical characteristics alone was determined by the analysis of deviance with generalized linear modeling (GLM). The clinical characteristics were coded as a binary indication, and, depending on the finding, the genetic markers were coded by a dominant scheme, a recessive scheme, or a scheme that assumed a continuous contribution by genotype: (aa, aA, AA)=(1, 0.5, 0). Identified genetic marker and clinical characteristic interactions were explicitly represented in the GLM model.

Additionally, in NTRK2, for which multiple SNPs were identified, haplotype-based analyses were done using a sliding window of two or three SNPs across the gene using the COCAPHASE program. Using COCAPHASE, the significance of the haplotype analysis findings was estimated with a separate permutation analysis.

Table 2 illustrates the demographic features of the subjects studied. The responder group was significantly older than the non-responder group. There were more women than men in the sample, but this did not differ significantly between response groups.

TABLE 2

Demographic Features of Subjects

| | Lithium Responders | Lithium Non-Responders |
|---|---|---|
| N | 92 | 92 |
| Age[1] | 46.3 ± 12.9 | 40.6 ± 11.5 |
| Gender (M:F)[2] | 33:59 | 41:51 |

[1]Mean ± SD; t = 2.8, p = 0.002
[2]NS
[3]Median ± SD; NS, Mann-Whitney U test

Eight clinical characteristics were examined for their relationship to lithium response. Table 3 summarizes those characteristics that yielded nominal significance. Consistent with previous literature, the presence of dysphoric mania was significantly associated with poor response to lithium, occurring twice as frequently amongst non-responders as compared to responders ($\chi 2 = 10.8$, 1 df, p*=0.001, q=0.0047). Also agreeing with prior findings, rapid cycling was also significantly associated with poor response to lithium ($\chi 2 = 5.6$, 1 df, p*=0.02, q=0.041). Not surprisingly, these two clinical variables were highly correlated with each other. Dysphoric mania was more than twice as frequent among subjects with rapid cycling, occurring in 49% of those with rapid cycling compared with 21% of those without rapid cycling. ($\chi 2 = 15.5$, 1 df, p=0.00008).

TABLE 3

Relationship between Clinical Features of Bipolar Disorder and Response to Lithium

| | Lithium responders | Lithium Non-Responders | p[1] | p*[2] | q[3] | $P_b$*[4] |
|---|---|---|---|---|---|---|
| N | 92 | 92 | | | | |
| Dysphoric mania | 20 (22%) | 41 (45%) | 0.001 | 0.001 | 0.0047 | 0.008 |
| Bipolar I | 78 (85%) | 75 (82%) | NS | NS | NS | NS |
| Rapid Cycling | 32 (35%) | 48 (52%) | 0.017 | 0.018 | 0.041 | NS |
| History of Suicide Attempt | 57 (62%) | 55 (60%) | NS | NS | NS | NS |
| PTSD | 7 (7.6%) | 17 (18.5%) | 0.028 | 0.029 | 0.045 | NS |
| Panic Attacks | 30 (33%) | 40 (43%) | NS | NS | NS | NS |
| Panic Disorder | 20 (22%) | 24 (26%) | NS | NS | NS | NS |

TABLE 3-continued

Relationship between Clinical Features of Bipolar Disorder and Response to Lithium

| | Lithium responders | Lithium Non-Responders | $p^1$ | $p^{*2}$ | $q^3$ | $P_b^{*4}$ |
|---|---|---|---|---|---|---|
| Alcohol or Substance Dependence | 36 (39%) | 44 (48%) | NS | NS | NS | NS |

[1] All analyses have 1 degree of freedom.
[2] Permutation method applied to 8 clinical hypothesis tests
[3] FDR method by Storey applied to 8 clinical hypothesis tests
[4] Bonferroni method applied to 8 clinical hypothesis tests
NS, not significant Post-traumatic stress disorder (PTSD) was more than twice as common among non-responders compared to responders, though the number of subjects was small ($\chi2=4.8$, 1 df, $p^*=0.029$, $q=0.045$). Such an association of lithium non-response with PTSD has not been previously reported.

Consistent with previous literature, these results suggest a distinct, and possibly more severe, phenotype in lithium non-responders. It was hypothesized that distinct pathophysiological processes might underlie these subforms of illness, and that different genes might influence response to lithium in one form as opposed to the other. For this reason, the genetic marker analysis by subjects with euphoric mania and no rapid cycling versus all other subjects were stratisfied.

Ninety-six genetic markers were originally selected in nine genes. Assays could be designed for 89 of these. The 5-HT-TLPR polymorphism demonstrated almost no diversity over this data set. Eighty SNPs with genotypic distributions consistent with Hardy-Weinberg equilibrium were available for testing after removing non-polymorphic SNPs from the data set. Sixty-Seven of the SNPs (Table 4) had sufficient cell frequencies to undergo high-level "data mining." Tests for either a trend in genotype (continuous) or a dominant allelic association with lithium response were conducted in the context of the presence of either of two comorbid indications, dysphoric mania or rapid cycling. Six SNPs in five genes were nominally significant before accounting for multiple comparisons, and they remained significant after (Table 5).

TABLE 4

Genetics Markers Tested

| Gene | Variants | Function | Chromosomal Location | Gene size (kb) | Density (Kb/SNP) |
|---|---|---|---|---|---|
| BDNF | 7 | Neuronal growth factor | 11p13 | 66 | 9.4 |
| NTRK2 | 25 | Receptor for BDNF | 9q22.1 | 208 | 8.3 |
| GRK3 | 4 | Receptor desensitization | 22q12.1 | 158 | 39.5 |
| GSK3B | 4 | Wnt signaling | 3q13.3 | 267 | 66.8 |
| IMPA1 | 5 | Inositol turnover | 8q21 | 28 | 5.6 |
| IMPA2 | 11 | Inositol turnover | 18p11.2 | 49 | 4.5 |
| INPP1 | 7 | Inositol turnover | 2q32 | 12 | 1.7 |
| MARCKS | 4 | Membrane trafficking | 6q22.2 | 4 | 1 |
| Total | 67 | | | | |

TABLE 5

Associations between Lithium Response and Genetic Markers, Accounting for Euphoric/Dysphoric Mania

| Gene | Marker | Location | Genotype Coding Scheme | $p^1$ | $p^{*4}$ | $q^5$ | $P_b^{*6}$ |
|---|---|---|---|---|---|---|---|
| GRK3 | C2190077 | Intronic | Continuous | 0.006 | $0.02^2$ | $0.02^2$ | $NS^2$ |
| NTRK2 | rs1387923 | Downstream | Continuous | 0.0015 | $0.005^2$ | $0.007^2$ | $0.045^2$ |
| NTRK2 | rs1565445 | Intronic | Dominant allele | 0.033 | $NS^3$ | $0.04^3$ | $NS^3$ |
| GSK3B | rs2199503 | Intronic | Continuous | 0.019 | $0.05^2$ | $0.03^2$ | $NS^2$ |
| IMPA2 | rs971363 | Upstream | Dominant allele | 0.015 | $0.05^3$ | $0.03^3$ | $NS^3$ |
| INPP1 | rs2067421 | Intronic | Dominant allele | 0.035 | $NS^3$ | $0.04^3$ | $NS^3$ |

[1] All analyses have 1 degree of freedom and were stratified by a constructed variable indicating the presence of either dysphoric mania or rapid cycling.
[2] Multiple test comparisons adjusted using 8 clinical and 32 genotype tests for trend.
[3] Multiple test comparisons adjusted using 8 clinical and 32 genotype tests for 38 tests for a dominant effect.
[4] Permutation method was used.
[5] FDR method by Storey was used.
[6] Bonferroni method was used.
NS, not significant While indicating that a SNP has an association with lithium response in one or both of the strata tested, the tests reported in Table 5 do not indicate in which strata the SNP was significant or the specific form of the association. To accomplish this, subsequent tests were performed on the two most significant SNPs, rs1387923 in NTRK2 (p=0.0015, p*=0.005, q=0.007) and rs133845 in GRK3 (p=0.006, p*=0.02, q=0.02) (see table 1 for respective sequences).

The response rates for the rs1387923 SNP in NTRK2 exhibited a "dose" response type effect only in subjects with euphoric mania (FIG. 1). Subjects with euphoric mania had a response rate of 34%, 62%, and 83% if they had 0, 1, or 2 copies of the minor allele (C), respectively. For subjects with dysphoric mania, genotype had no relationship to response rate. A three-way contingency table analysis of response, dysphoric mania, and the rs1387923 allele using log-linear analysis yielded a highly significant association ($\chi2=34$, 4 df, p=10-6). An allele-wise analysis using the program COCAPHASE yielded a consistent result with an odds ratio of 2.5 (p=0.0005) (Table 6). An adjusted p-value of 0.029 was obtained when all 28 SNPs examined within the NTRK2 gene were considered. Analysis of deviance indicated that the NTRK2 SNP genotype had a significant effect on the lithium response rate over that of the effect due to dysphoric mania alone ($\chi2=7.5$, 1 df, p=0.006).

TABLE 6

Allele-wise association of NTRK2 lithium response in euphoric mania

| rs1387923 | Non-responders | Responders | |
|---|---|---|---|
| C Allele | 34 (33%) | 80 (55%) | 114 |
| T Allele | 68 (66%) | 64 (45%) | 132 |
| | 102 | 144 | |

OR = 2.5,
p = 0.0005
OR, odds ratio

Figure 2:
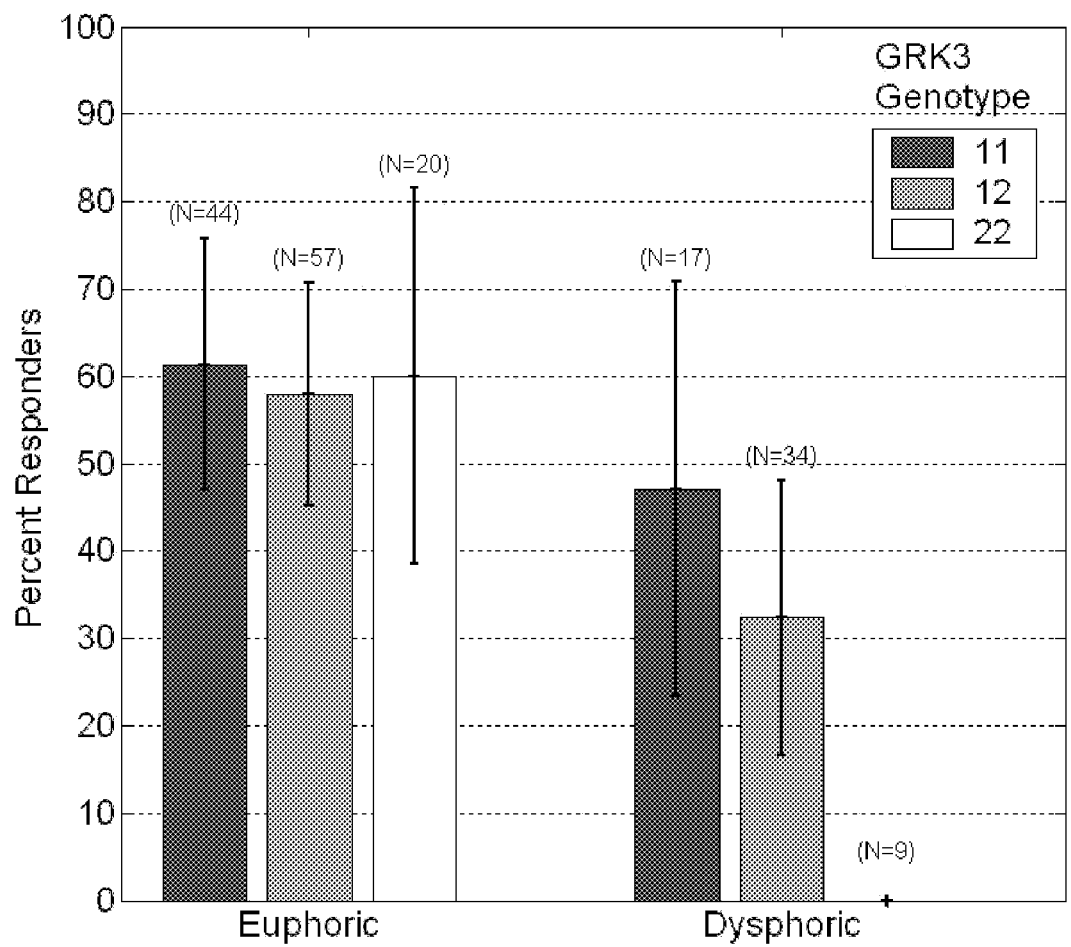
FIG. 2 shows that a GRK3 genotype is associated with lithium response in dysphoric mania. GRK3 genotypes AA, AC, CC in rs133845 are minor homozygote, heterozygote and major homozygote, respectively.

The response rates for the rs133845 SNP in GRK3, also exhibited a "dose" response effect, but only for subjects with dysphoric mania (FIG. 2). Analysis of deviance indicated that the GRK3 SNP genotype made a statistically significant contribution to the NTRK2 genotype and euphoric mania in predicting response ($\chi2=10.5$, 1 df, p=0.001). Combined, these two SNPs had a significant effect on the lithium response rate while accounting for dysphoric mania when compared to the effect of dysphoric mania on lithium response alone ($\chi2=18.2$, 2 df, p=1.1×10-4).

Because of the correlation between dysphoric mania and rapid cycling, whether rapid cycling could add any statistically significant explanatory power to dysphoric mania alone or to the interaction between the NTRK2 and GRK3 genotypes with dysphoric mania was also examined. Analysis of deviance indicated that rapid cycling did not provide significant information over dysphoric mania alone ($\chi2=2.3$, 1 df, p=0.12), and that it did not provide additive information over the interaction identified between NTRK2, GRK3, and dysphoric mania.

The invention provides an association of a series of clinical variables (Table 3) and genetic markers in nine candidate genes (Table 4) in order to identify clinical and genetic factors associated with therapeutic response to lithium. Three clinical variables were associated with good lithium response (Table 3): predominance of euphoric mania, absence of rapid cycling and absence of PTSD. Markers in five genes were associated with lithium response with nominal significance (Table 5). The most strongly associated was a SNP (rs1387923) near the 3' end of the NTRK2 gene, followed by a SNP (rs133845) in GRK3. In subjects with dysphoric mania, The association between the NTRK2 SNP genotype and lithium response was observed in euphoric subjects, whereas the association between the GRK3 SNP genotype and response was observed in dysphoric subjects.

Based on the FWER and FDR measures and post association test analyses, dysphoric mania and the NTRK2 and GRK3 SNPs play a role in lithium response. Both the "gold standard" FWER permutation analysis and the FDR analysis indicated that there was a maximum 2% chance that one of the factors was a false positive. Analysis of deviance showed that the interaction of the two SNPs and dysphoric mania had a significant effect on the lithium response rate above that of dysphoric mania alone, ($\chi2=18.2$, 2 df, p=1.1E-4, pb*=0.008). A three-way contingency table analysis showed that the three factors of NTRK2 rs1387923 and dysphoric mania with lithium response is significant ($\chi2=32$, 7 df, p=10-6, pb*<10-4). The FWER Bonferroni adjusted pb* values indicate that there is a low probability (8/1000) that the SNPs are not more informative than dysphoric mania alone for lithium response, and that the total interaction is uninformative (1/10,000).

When considered as an independent factor, rapid cycling has a significant association with lithium response. However, rapid cycling is strongly correlated with dysphoric mania ($\chi2=12.9$, p=3.3×10-4). While the trend is significant overall, the dominant effect is due to dysphoric mania. When stratified by dysphoric mania, rapid cycling does not have a statistically significant association with lithium response (p=0.12). Dysphoric mania however, after stratifying by rapid cycling, still shows a statistically significant association to lithium response (p=0.006). Analysis of deviance also shows that rapid cycling does not add information to the interaction of dysphoric mania and the two NTRK2 and GRK3 SNPs with lithium response.

The other genetic markers (GSK3B, IMPA2, and INPP1) had marginally significant p-values and also marginal q-values. The FDR q-value analysis indicated that 1 of the set of 7 significant factors was likely a false positive.

Two genes were examined here that have been reported to be associated with lithium response in previous reports. Serretti et al. reported association of 5-HTTLPR with prospectively determined prophylactic response to lithium in bipolar disorder and unipolar disorder. In the study herein, 5-HTTLPR had very low diversity, and showed no evidence of association with response. Their sample did also include patients with unipolar depression, which represents a difference in samples examined. Steen et al., also reported association of response to the INPP1 gene in a small sample. However, as discussed, while some support for INPP1 was identified, it did not have a significant FWER p*-value. Very recently, lithium response has been also reported to be associated with the Val/Met polymorphism in the BDNF gene.

Many of these clinical variables and genetic markers are not independent of each other. The markers within the same genes are in varying degrees of linkage disequilibrium, and rapid cycling and dysphoric mania are highly correlated with each other. The interaction effects observed between genetic markers and clinical variables represent another source of non-independence. Eight clinical variables and 70 genetic markers were tested in the context of two clinical parameters.

To account for the dependency of lithium response on clinical characteristics while testing for associations between lithium response and genetic markers, the genetic markers tests were stratified by a constructed clinical variable. The constructed variable represented the two correlated clinical variables dysphoric mania and rapid cycling as neither, either, or both factors.

To account for the multiple tests conducted, FWER measures were used to assess the probability that there were one or more false positives in a set of factors deemed significant. The Bonferroni method, while most suitable for application to independent factors, is commonly being applied to genetic analysis and was calculated for reference.

The permutation based FWER assessment, however, is a good choice to evaluate multiple genetic association tests. The dependent nature of the genetic and the clinical data are preserved with the permutation method, and they are appropriately accounted for in the composite null distribution that is used to compute the FWER global p*-values. This method was applied to each of the three sequential sets of tests to obtain adjusted p*-values for their composite null hypothesis distributions.

Additionally, to assess the significance of the findings in the context of multiple comparisons in a less computationally intensive manner, FDR q-value analysis was also performed. The FDR is the expected value of the ratio of number of false positive features to the number of significant features, and provides a means of assessing the overall accuracy of a set of significant features. The q-value is a measure of significance for that feature like the p-value, but the q-value for a particular feature is the expected proportion of false positives incurred when calling that feature significant. The joint assessment of these methods allows a rigorous interpretation of the statistical findings in the study.

In addition to such statistical aspects, the relationship of the NTRK2 and GSK3 genotypes to clinical parameter and response illustrated in FIGS. 1 and 2 makes compelling biological and clinical sense.

The association to NTRK2 provides further support for the role of the BDNF/trkb signaling system in lithium response. The NTRK2 gene codes for the trkb tyrosine kinase receptor, which is the receptor for BDNF. Activation of trkb leads to the activation of a number of signaling pathways including PI-3 kinase leading to an increase in PIP3. Akt is a primary target which in turn phosphorylates GSK3b, a gene inhibited by lithium. BDNF expression is induced by lithium and antidepressants. BDNF also has been shown to have an antidepressant-like effect when injected into hippocampus in behavioral models of depression. Together, these data indicate the importance of the BDNF/trkb system in lithium action, and of variation in these genes in response.

An intriguing aspect of the results is the interaction of genotypes with clinical presentation. Clinical experiences with patients who have a robust response to lithium, as well as systematic research, indicate that these patients have a unique clinical profile, including absence of dysphoric mania, mixed states, and rapid cycling, as well as later age of onset, less comorbidity, and a stronger family history of bipolar disorder. Together these observations have led to the hypothesis that lithium responders may comprise a distinct form of illness with different biology and genetics. The results are consistent with this idea and suggest that different genes in different signaling pathways may be aberrant in lithium responders vs. non-responders. They further argue for the importance of incorporating clinical subtype in pharmacogenetic studies.

Similarly, these results suggest that euphoric vs. dysphoric mania may result from genetically distinct pathophysiologies. A possible explanation for the interaction with mania subtype is that the disease process in dysphoric mania does not involve the BDNF/Trkb pathway. If lithium's action is at least in part mediated through this pathway, then lithium has limited therapeutic benefit because it does not normalize the defective signaling. Similarly, variation in the NTRK2 gene has little predictive value because that pathway is not involved. An analogous argument could be made for GRK3, that dysphoric mania results in part from defects in receptor desensitization. The distinction between euphoric and dysphoric mania has received limited attention in terms of genetic studies. These results suggest that it may be a useful clinical parameter for stratifying samples in genetic studies, as well as, exploring the role of specific candidate genes.

A number of embodiments have been described. Nevertheless, it will be understood that various modifications may be made without departing from the spirit and scope of the description. Accordingly, other embodiments are within the scope of the following claims.

What is claimed is:

1. A method comprising:
   (a) providing a sample comprising polynucleotides obtained from a human subject having a bipolar disorder;
   (b) contacting the sample with at least one probe comprising at least 8 contiguous nucleotides of a sequence selected from the group consisting of SEQ ID NO:7 or 8 and comprising the nucleotide at position 26 or the complement thereof; and
   (c) detecting a polynucleotide molecule having a C allele corresponding to position 26 of SEQ ID NO:7 or 8 and
   (d) identifying the subject as responsive to lithium for treatment of the bipolar disorder with euphoric mania when the subject has a C allele corresponding to position 26 of SEQ ID NO:7 or 8.

2. The method of claim 1, wherein the probe comprises nucleotides 25-27 of SEQ ID NO:7 or 8.

3. The method of claim 1, wherein the at least one probe comprising at least 8 contiguous nucleotides of SEQ ID NO:8 and containing nucleotide 26.

4. The method of claim 1, further comprising contacting the sample with at least one additional probe comprising 8 contiguous nucleotides selected from SEQ ID NO: 1-6 and 9-16 and containing nucleotide 26.

5. The method of claim 1, wherein the probe comprises nucleotide 26 of SEQ ID NO:7 or 8 at the 5' or 3' end.

6. A method for determining whether a human subject having a mental or mood disorder comprising euphoric mania is responsive to lithium, comprising
   contacting a sample from the subject with at least one probe comprising at least 8 contiguous nucleotides of a sequence consisting of SEQ ID NO: 7 or 8 and comprising the nucleotide at position 26 or the complement thereof; detecting a C allele at position 26 or the complement thereof in the sample; and identifying that a subject has an increased response to lithium for mood stabilization when the C allele at position 26 or the complement thereof is detected.

7. The method of claim 6, further comprising at least one additional probe comprises at least 8 contiguous nucleotides of SEQ ID NO: 1-6 and 9-16.

8. The method of claim 6, wherein the probe comprises nucleotides 25-27 of SEQ ID NO:7 or 8.

9. The method of claim 6, wherein the at least one probe comprising at least 8 contiguous nucleotides of SEQ ID NO:8 and containing nucleotide 26.

10. The method of claim 6, wherein the probe comprises nucleotide 26 of SEQ ID NO:7 or 8 at the 5' or 3' end.

11. The method of claim 1 or 6, further comprising identifying a symptom selected from the group consisting of euphoric mania, dysphoric mania, Bipolar I, Rapid Cycling, History of Suicide Attempt, PTSD, Panic Attacks/Panic Disorder, Alcohol or Substance Dependence, and any combination thereof.

12. The method of claim 11, wherein if the subject has primarily a lifetime history of euphoric mania and a polymorphism in neurotrophic tyrosine kinase, receptor, type 2 (NTRK2) comprising rs1387923 is indicative of a 34, 62, or 83% probability of responding well to lithium depending on whether subject has a CC, CT or TT genotype, respectively.

13. A method of determining a human subject's response to lithium comprising isolating a sample from a human subject; detecting a C allele at the SNP position of rs1387923 in the sample using a probe, wherein the presence of the C allele is indicative of the subject having increased responsiveness to lithium for mood stabilization compared to a subject lacking the C allele at the SNP position of rs1387923.

14. The method of claim 13, further comprising measuring a polymorphism comprising a sequence selected from the group consisting of SEQ ID NO: 1-6 and 9-16.

15. The method of claim 13, wherein the polymorphism is detected by a method selected from the group consisting of (a) a primer extension assay; (b) an allele-specific PCR assay; (c) a nucleic acid amplification assay; (d) a hybridization assay; (e) a mismatch-detection assay; (f) an enzymatic nucleic acid cleavage assay; and (g) a sequencing assay.

16. The method of claim 13, further comprising measuring a clinical symptom of the subject.

17. The method of claim 13, further comprising measuring a polymorphism in the GRK3 gene.

18. The method of claim 17, wherein the polymorphism comprises an A nucleotide at position 26 of SEQ ID NO:1 or 2.

19. The method of claim 13, wherein the polymorphism comprises a C nucleotide at position 26 of SEQ ID NO:7 or 8.

* * * * *

SEQUENCE LISTING

<160> NUMBER OF SEQ ID NOS: 16

<210> SEQ ID NO 1
<211> LENGTH: 51
<212> TYPE: DNA
<213> ORGANISM: Artificial Sequence
<220> FEATURE:
<223> OTHER INFORMATION: Human SNP (rs133845) in GRK3 gene

<400> SEQUENCE: 1
tctaactcct cagagagcac gtaaaacatg aatctaccct gtagttgctg t          51

<210> SEQ ID NO 2
<211> LENGTH: 51
<212> TYPE: DNA
<213> ORGANISM: Artificial Sequence
<220> FEATURE:
<223> OTHER INFORMATION: Human SNP (rs133845) in GRK3 gene

<400> SEQUENCE: 2
tctaactcct cagagagcac gtaaaccatg aatctaccct gtagttgctg t          51

<210> SEQ ID NO 3
<211> LENGTH: 51
<212> TYPE: DNA
<213> ORGANISM: Artificial Sequence

```
<220> FEATURE:
<223> OTHER INFORMATION: Human SNP (rs11913984) in GRK3

<400> SEQUENCE: 3
ttctcttatt tgatggaaat tttatctttt tacaaccca ttatcagttt g        51

<210> SEQ ID NO 4
<211> LENGTH: 51
<212> TYPE: DNA
<213> ORGANISM: Artificial Sequence
<220> FEATURE:
<223> OTHER INFORMATION: Human SNP (rs11913984) in GRK3 gene

<400> SEQUENCE: 4
ttctcttatt tgatggaaat tttatgtttt tacaaccca ttatcagttt g         51

<210> SEQ ID NO 5
<211> LENGTH: 51
<212> TYPE: DNA
<213> ORGANISM: Artificial Sequence
<220> FEATURE:
<223> OTHER INFORMATION: Human SNP (rs1187287) in NTRK2 gene

<400> SEQUENCE: 5
tagggacttg cgttggtaat gaataccatg gtttagatgt ttattgctgt a         51

<210> SEQ ID NO 6
<211> LENGTH: 51
<212> TYPE: DNA
<213> ORGANISM: Artificial Sequence
<220> FEATURE:
<223> OTHER INFORMATION: Human SNP (rs1187287) in NTRK2 gene

<400> SEQUENCE: 6
tagggacttg cgttggtaat gaatatcatg gtttagatgt ttattgctgt a         51

<210> SEQ ID NO 7
<211> LENGTH: 51
<212> TYPE: DNA
<213> ORGANISM: Artificial Sequence
<220> FEATURE:
<223> OTHER INFORMATION: Human SNP (rs1387923) in NTRK2 gene

<400> SEQUENCE: 7
tatatggcca aaccaaaggt caacactgaa aataaaagtc ctgagacagg g         51

<210> SEQ ID NO 8
<211> LENGTH: 51
<212> TYPE: DNA
<213> ORGANISM: Artificial Sequence
<220> FEATURE:
<223> OTHER INFORMATION: Human SNP (rs1387923) in NTRK2 gene

<400> SEQUENCE: 8
tatatggcca aaccaaaggt caacattgaa aataaaagtc ctgagacagg g         51

<210> SEQ ID NO 9
<211> LENGTH: 51
<212> TYPE: DNA
<213> ORGANISM: Artificial Sequence
<220> FEATURE:
<223> OTHER INFORMATION: Human SNP (rs1565445) in NTRK2 gene

<400> SEQUENCE: 9
aagcaggcaa aggtgtggct aaaaaccacc ttccaagtaa tgaggcagta c         51
```

```
<210> SEQ ID NO 10
<211> LENGTH: 51
<212> TYPE: DNA
<213> ORGANISM: Artificial Sequence
<220> FEATURE:
<223> OTHER INFORMATION: Human SNP (rs1565445) in NTRK2 gene

<400> SEQUENCE: 10
aagcaggcaa aggtgtggct aaaaatcacc ttccaagtaa tgaggcagta c          51

<210> SEQ ID NO 11
<211> LENGTH: 51
<212> TYPE: DNA
<213> ORGANISM: Artificial Sequence
<220> FEATURE:
<223> OTHER INFORMATION: Human SNP (rs1187352) in NTRK2 gene

<400> SEQUENCE: 11
acagtgagca agagtcagac aattcaggca taggcccctc tgccacctca c          51

<210> SEQ ID NO 12
<211> LENGTH: 51
<212> TYPE: DNA
<213> ORGANISM: Artificial Sequence
<220> FEATURE:
<223> OTHER INFORMATION: Human SNP (rs1187352) in NTRK2 gene

<400> SEQUENCE: 12
acagtgagca agagtcagac aattcgggca taggcccctc tgccacctca c          51

<210> SEQ ID NO 13
<211> LENGTH: 51
<212> TYPE: DNA
<213> ORGANISM: Artificial Sequence
<220> FEATURE:
<223> OTHER INFORMATION: Human SNP (rs971363) in IMPA2 gene

<400> SEQUENCE: 13
cggctggact ttataaactc ttcacaccca aaactcgaat ttggagacgg a          51

<210> SEQ ID NO 14
<211> LENGTH: 51
<212> TYPE: DNA
<213> ORGANISM: Artificial Sequence
<220> FEATURE:
<223> OTHER INFORMATION: Human SNP (rs971363) in IMPA2 gene

<400> SEQUENCE: 14
cggctggact ttataaactc ttcaccccca aaactcgaat ttggagacgg a          51

<210> SEQ ID NO 15
<211> LENGTH: 51
<212> TYPE: DNA
<213> ORGANISM: Artificial Sequence
<220> FEATURE:
<223> OTHER INFORMATION: Human SNP (rs915) in IMPA1 gene

<400> SEQUENCE: 15
atcactccct accttgaaaa ctttacagaa gcatttttaa ttttacaaca c          51

<210> SEQ ID NO 16
<211> LENGTH: 51
<212> TYPE: DNA
<213> ORGANISM: Artificial Sequence
<220> FEATURE:
<223> OTHER INFORMATION: Human SNP (rs915) in IMPA1 gene
```

-continued

```
<400> SEQUENCE: 16
atcactccct accttgaaaa ctttatagaa gcatttttaa ttttacaaca c          51
```